US007838447B2

(12) United States Patent  (10) Patent No.: US 7,838,447 B2
Clark et al.  (45) Date of Patent: Nov. 23, 2010

(54) ANTIMICROBIAL PRE-MOISTENED WIPERS

(75) Inventors: James W. Clark, Roswell, GA (US);
Shawn E. Jenkins, Duluth, GA (US);
Julie W. Trusock, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 79 days.

(21) Appl. No.: 10/027,791

(22) Filed: Dec. 20, 2001

(65) Prior Publication Data
US 2003/0194932 A1 Oct. 16, 2003

(51) Int. Cl.
*B32B 5/02* (2006.01)
*B32B 27/04* (2006.01)
*B32B 27/12* (2006.01)
*B32B 9/00* (2006.01)
*B32B 9/04* (2006.01)

(52) U.S. Cl. .......................... 442/123; 442/59; 442/152; 442/153

(58) Field of Classification Search ................ 424/404; 510/382; 442/59–180
See application file for complete search history.

(56) References Cited

U.S. PATENT DOCUMENTS

| | | | |
|---|---|---|---|
| 428,267 A | 5/1890 | Romano, III, et al. |
| 3,338,992 A | 8/1967 | Kinney |
| 3,341,394 A | 9/1967 | Kinney |
| 3,494,821 A | 2/1970 | Evans |
| 3,502,538 A | 3/1970 | Peterson |
| 3,502,763 A | 3/1970 | Hartman |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,855,046 A | 12/1974 | Hansen et al. |
| 4,100,324 A | 7/1978 | Anderson et al. |
| 4,117,187 A | 9/1978 | Adams et al. |
| 4,144,370 A | 3/1979 | Boulton |
| 4,282,366 A | 8/1981 | Eudy |
| 4,340,563 A | 7/1982 | Appel et al. |
| 4,374,888 A | 2/1983 | Bornslaeger |
| 4,406,892 A | 9/1983 | Eudy |
| 4,597,887 A | 7/1986 | Colodney et al. |
| 4,601,081 A | 7/1986 | Sutton et al. |
| 4,615,937 A | 10/1986 | Bouchette |
| 4,643,939 A | 2/1987 | Sugiyama et al. |
| 4,659,609 A | 4/1987 | Lamers et al. |
| 4,692,374 A | 9/1987 | Bouchette |
| 4,737,405 A | 4/1988 | Bouchette |
| 4,740,398 A | 4/1988 | Bouchette |
| 4,741,944 A | 5/1988 | Jackson et al. |
| 4,745,132 A | 5/1988 | Swered et al. |
| 4,775,582 A | 10/1988 | Abba et al. |
| 4,781,974 A | 11/1988 | Bouchette et al. |
| 4,795,668 A | 1/1989 | Krueger et al. |
| 4,804,492 A | 2/1989 | Bernarducci |
| 4,833,003 A | 5/1989 | Win et al. |
| 4,837,079 A | 6/1989 | Quantrille et al. |
| 4,839,373 A | 6/1989 | Ito et al. |
| 4,847,088 A | 7/1989 | Blank |
| 4,921,701 A | 5/1990 | Blank |
| 4,929,498 A | 5/1990 | Suskin et al. |
| 4,941,989 A | 7/1990 | Kramer et al. |
| 4,998,984 A | 3/1991 | McClendon |
| 5,049,440 A | 9/1991 | Bornhoeft, III et al. |
| 5,057,368 A | 10/1991 | Largman et al. |
| 5,061,395 A | 10/1991 | Meng |
| 5,069,970 A | 12/1991 | Largman et al. |
| 5,091,102 A | 2/1992 | Sheridan |
| 5,108,820 A | 4/1992 | Kaneko et al. |
| 5,139,781 A | 8/1992 | Birtwistle et al. |
| 5,141,803 A | 8/1992 | Pregozen |
| 5,145,596 A | 9/1992 | Blank et al. |
| 5,162,074 A | 11/1992 | Hills |
| 5,169,625 A | 12/1992 | Blank |
| 5,277,976 A | 1/1994 | Hogle et al. |
| 5,284,703 A | 2/1994 | Everhart et al. |
| 5,290,482 A | 3/1994 | Marschner et al. |
| 5,300,167 A | 4/1994 | Nohr et al. |

(Continued)

FOREIGN PATENT DOCUMENTS

EP 0259249 7/1987

(Continued)

OTHER PUBLICATIONS

Abstract of Japanese Patent No. 10127516, May 19, 1998.

(Continued)

*Primary Examiner*—Rena L Dye
*Assistant Examiner*—Jennifer Steele
(74) *Attorney, Agent, or Firm*—Dority & Manning, P.A.

(57) ABSTRACT

A pre-moistened wiper that exhibits good antimicrobial kill at relatively small levels of antimicrobial agent is provided. In one embodiment, for example, the wiper contains a sanitizing formulation that includes between about 0.01% by weight to about 1% by weight of an antimicrobial agent, including a quaternary ammonium compound, and water. The sanitizing formulation is capable of being released from the wiper as a solution such that the quaternary ammonium compound is present within the solution in an amount less than about 2000 parts per million of the solution. The wiper can exhibit a log reduction for *E. Coli* of at least about 2.

18 Claims, No Drawings

U.S. PATENT DOCUMENTS

| | | | |
|---|---|---|---|
| 5,320,805 A | 6/1994 | Kramer et al. | |
| 5,336,552 A | 8/1994 | Strack et al. | |
| 5,342,534 A | 8/1994 | Skrobala et al. | |
| 5,350,624 A | 9/1994 | Georger et al. | |
| 5,382,400 A | 1/1995 | Pike et al. | |
| 5,403,587 A | 4/1995 | McCue et al. | |
| 5,421,898 A | 6/1995 | Cavanagh | |
| 5,424,323 A | 6/1995 | Wachman et al. | |
| 5,435,935 A | 7/1995 | Kupneski | |
| 5,466,410 A | 11/1995 | Hills | |
| 5,514,640 A | 5/1996 | Jones et al. | |
| 5,531,984 A | 7/1996 | Staats | |
| 5,567,372 A | 10/1996 | Nohr et al. | |
| 5,569,732 A | 10/1996 | Smith | |
| 5,620,779 A | 4/1997 | Levy et al. | |
| 5,656,361 A | 8/1997 | Vogt et al. | |
| 5,700,842 A | 12/1997 | Cole | |
| 5,705,532 A | 1/1998 | Modak et al. | |
| D390,708 S | 2/1998 | Brown | |
| 5,762,948 A | 6/1998 | Blackburn et al. | |
| 5,777,010 A | 7/1998 | Nohr et al. | |
| 5,783,146 A | 7/1998 | Williams, Jr. | |
| 5,785,179 A | 7/1998 | Buczwinski et al. | |
| 5,827,870 A | 10/1998 | Chodosh | |
| 5,853,641 A | 12/1998 | Nohr et al. | |
| 5,853,883 A | 12/1998 | Nohr et al. | |
| 5,854,147 A | 12/1998 | Nohr et al. | |
| 5,863,663 A | 1/1999 | Mackey et al. | |
| 5,871,763 A | 2/1999 | Luu et al. | |
| 5,888,524 A | 3/1999 | Cole | |
| 5,919,471 A | 7/1999 | Saferstein et al. | |
| 5,929,016 A | 7/1999 | Harrison | |
| 5,935,883 A | 8/1999 | Pike | |
| 5,962,112 A | 10/1999 | Haynes et al. | |
| 5,964,351 A | 10/1999 | Zander | |
| 5,989,004 A | 11/1999 | Cook | |
| 6,015,816 A | 1/2000 | Kostyniak et al. | |
| 6,030,331 A | 2/2000 | Zander | |
| 6,042,877 A | 3/2000 | Lyon et al. | |
| 6,080,387 A | 6/2000 | Zhou et al. | |
| 6,090,771 A | 7/2000 | Burt et al. | |
| 6,093,665 A | 7/2000 | Sayovitz et al. | |
| 6,103,061 A | 8/2000 | Anderson et al. | |
| 6,107,261 A | 8/2000 | Taylor et al. | |
| 6,120,784 A | 9/2000 | Snyder, Jr. | |
| 6,136,770 A * | 10/2000 | Cheung et al. | 510/384 |
| 6,158,614 A | 12/2000 | Haines et al. | |
| 6,197,322 B1 | 3/2001 | Dutkiewicz et al. | |
| 6,197,404 B1 | 3/2001 | Varona | |
| 6,197,738 B1 | 3/2001 | Regutti | |
| 6,200,669 B1 | 3/2001 | Marmon et al. | |
| 6,207,596 B1 | 3/2001 | Rourke et al. | |
| 6,214,363 B1 | 4/2001 | Beerse et al. | |
| 6,269,969 B1 | 8/2001 | Huang et al. | |
| 6,269,970 B1 | 8/2001 | Huang et al. | |
| 6,273,359 B1 | 8/2001 | Newman et al. | |
| 6,281,182 B1 | 8/2001 | Leonard et al. | |
| 6,284,259 B1 | 9/2001 | Beerse et al. | |
| 6,284,723 B1 | 9/2001 | Zhou et al. | |
| 6,313,049 B1 | 11/2001 | Heady et al. | |
| 6,315,864 B2 | 11/2001 | Anderson et al. | |
| 6,656,456 B2 * | 12/2003 | Dodd et al. | 424/67 |
| 6,667,289 B2 * | 12/2003 | Harrison et al. | 510/384 |
| 6,667,290 B2 | 12/2003 | Svendsen | |
| 6,716,805 B1 * | 4/2004 | Sherry et al. | 510/295 |
| 2002/0031486 A1 * | 3/2002 | Lunsmann et al. | 424/70.28 |
| 2002/0103098 A1 * | 8/2002 | Harrison et al. | 510/382 |
| 2002/0189040 A1 | 12/2002 | Svendsen | |
| 2003/0054970 A1 | 3/2003 | Svendsen | |

FOREIGN PATENT DOCUMENTS

| | | |
|---|---|---|
| EP | 0619074 A1 | 3/1994 |
| EP | 0639636 A2 | 2/1995 |
| EP | 0639636 A3 | 2/1995 |
| EP | 0869216 A1 | 10/1998 |
| EP | 1059032 A1 | 12/2000 |
| EP | 0796315 B1 | 8/2001 |
| EP | 00808151 | 8/2001 |
| EP | 1153544 A2 | 11/2001 |
| EP | 1153544 A3 | 11/2001 |
| WO | WO 9624329 | 8/1996 |
| WO | WO 9855094 | 12/1998 |
| WO | WO 9855096 | 12/1998 |
| WO | WO 9932697 | 7/1999 |
| WO | WO 9937200 | 7/1999 |
| WO | WO 9937858 | 7/1999 |
| WO | WO 0000026 | 1/2000 |
| WO | WO 0015897 | 3/2000 |
| WO | WO 0027191 | 5/2000 |
| WO | WO 0061105 | 10/2000 |
| WO | WO 0061106 | 10/2000 |
| WO | WO 0064408 | 11/2000 |
| WO | WO 0071183 A1 | 11/2000 |
| WO | WO 0071662 A1 | 11/2000 |
| WO | WO 0071789 A1 | 11/2000 |
| WO | WO 0100782 A1 | 1/2001 |
| WO | WO 0121138 A1 | 3/2001 |
| WO | WO 0123511 A1 | 4/2001 |
| WO | WO 012508 A1 | 2/2004 |

OTHER PUBLICATIONS

PCT Search Report, May 8, 2003.
Once Overs® Premoistened Bathroom Cleaning Wipes.
Pamphlet of Sani-Wipe™ The Ultimate in Food Safety Protection™.
U.S. EPA Pesticide Registration Report—Dated: Apr. 5, 2001—6 Pages.

* cited by examiner

ANTIMICROBIAL PRE-MOISTENED WIPERS

BACKGROUND OF THE INVENTION

Saturated or pre-moistened paper and textile wipers have been used in a variety of wiping and polishing cloths. These substrates are often provided in a sealed container and retrieved therefrom in a moist or saturated condition (i.e., pre-moistened). The pre-moistened cloth or paper wiper releases the retained liquid when used to clean or polish the desired surface.

Some pre-moistened wipers have been incorporated with antimicrobial agents in an attempt to kill microbes present on the surface being wiped. However, problems with such antimicrobial wipers often arise in the context of the food service industry. In particular, solutions released by wipers used in food service environments are often required to contain a relatively small amount of antimicrobial agent. For example, Title 21, Section 178.1010 of the United States Code of Federal Regulations sets forth various requirements for use of sanitizing solutions used on food-processing equipment, utensils, and other food-contact articles. Conventionally, it has been difficult to form food service wipers that release a relatively small amount of antimicrobial agent, yet still achieve the desired antimicrobial kill.

As such, a need currently exists for an improved pre-moistened wiper that is capable of achieving good antimicrobial kill at a relatively low level of released antimicrobial agent.

SUMMARY OF THE INVENTION

In accordance with one embodiment of the present invention, a wiper is provided that comprises a substrate (e.g., woven, nonwoven, wet-strength paper, etc.). A sanitizing formulation is applied to the substrate in an amount from about 150% to about 600% of the dry weight of the wiper. In one embodiment, the sanitizing formulation comprises between about 0.01% by weight to about 1% by weight of an antimicrobial and water. The sanitizing formulation is capable of being released from the substrate as a solution such that the quaternary compound is present within the solution in an amount less than about 2000 parts per million of the solution.

For example, in one embodiment, the antimicrobial agent may contain a quaternary ammonium compound, such as those having the following formula:

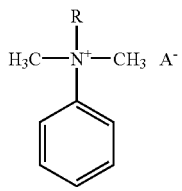

wherein,

R is a $C_8$-$C_{18}$ alkyl group; and

A is a halogen atom.

In some embodiments, the sequestrant may be selected from the group consisting of ethylenediamines, ethylenediaminetetraacetic acids and salts thereof, citric acids and salts thereof, glucuronic acids and salts thereof, polyphosphates, organophosphates, and dimercaprols. For example, in one embodiment, the sequestrant comprises ethylenediaminetetraacetic acid or salts thereof.

As stated, the sanitizing formulation may, in some embodiments, contain a surfactant. For example, in one embodiment, the surfactant comprises a nonionic surfactant, such as ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with amines, condensation products of ethylene oxide with amides, condensation products of ethylene oxide with alcohols, or mixtures thereof. In one embodiment, the nonionic surfactant comprises the product of a secondary aliphatic alcohol containing between about 8 to about 18 carbon atoms condensed with about 5 to about 30 moles of ethylene oxide.

In addition, the sanitizing formulation may also contain various other ingredients. For example, in some embodiments, the sanitizing formulation further comprises between about 0.001% to about 30% by weight of non-aqueous solvent, such as glycols, alcohols, or combinations thereof. In one embodiment, the non-aqueous solvent includes a blend of ethanol and propylene glycol. Moreover, the sanitizing formulation may also contain between about 0.001% to about 5% by weight of preservative, such as benzoic esters.

The pH of the sanitizing formulation may generally vary depending on a variety of different factors. For example, the pH of the formulation may, in some embodiments, be greater than about 8, and in some embodiments, between about 9 to about 12.

As a result of the present invention, it has been determined that the sanitizing formulation of the present invention can provide a log reduction for *S. aureus* (gram positive) and/or *E. coli* (gram negative) of at least about 2, in some embodiments at least about 3, in some embodiments at least about 4, and in some embodiments, at least about 5. Moreover, the wiper can also exhibit a Kill Efficiency Ratio of at least about 10, in some embodiments at least about 40, in some embodiments at least about 100, and in some embodiments, at least about 200. Further, the Antimicrobial Reduction can be less than about 95%, and in some embodiments, between about 60% to about 80%.

In another embodiment of the present invention, a method for sanitizing a surface is provided. The method includes providing a wiper that contains a substrate applied with a sanitizing formulation in an amount from about 150% to about 600% of the dry weight of the wiper. The sanitizing formulation comprises between about 0.01% by weight to about 0.4% by weight of at least one quaternary ammonium compound. In addition, the method also includes moving the wiper across the surface such that at least a portion of the sanitizing formulation is released from the wiper to form a released solution. The released solution contains less than about 2000 parts per million of the quaternary ammonium compound, and in some embodiments, between about 150 to about 450 parts per million of the quaternary ammonium compound. In this particular embodiment of the present invention, the released solution exhibits a log reduction for *E. Coli* of at least about 2.

Other features and aspects of the present invention are discussed in greater detail below.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

Definitions

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns.

As used herein, the term "meltblown fibers" refers to fibers formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonded fibers" refers to small diameter substantially continuous fibers that are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

As used herein, "through air bonding" or "TAB" means a process of bonding a nonwoven, for example, a multicomponent fiber web, in which air which is sufficiently hot to melt one of the polymers of which the fibers of the web are made is forced through the web. The melting and resolidification of the polymer provides the bonding.

As used herein, "ultrasonic bonding" means a process performed, for example, by passing the fabric between a sonic horn and anvil roll as illustrated in U.S. Pat. No. 4,374,888 to Bornslaeger, which is incorporated herein in its entirety by reference thereto for all purposes.

As used herein, the term "fiber" refers to an elongated extrudate formed by passing a polymer through a forming orifice such as a die. Unless noted otherwise, the term "fibers" includes discontinuous strands having a definite length and continuous strands of material, such as filaments.

DETAILED DESCRIPTION

In general, the present invention is directed to a wiper that is effective against gram negative and/or positive bacteria. In particular, the wiper of the present invention is applied with a sanitizing formulation that contains an antimicrobial agent such that, when released from the wiper during use, kills and/or inhibits the growth of bacteria on a surface. Unexpectedly, it has been discovered that the desired level of antimicrobial effectiveness can even be achieved at relatively small levels of the antimicrobial agent. Various embodiments of the present invention will now be described in more detail.

I. Wiper

The wiper of the present invention generally contains a substrate, such as an absorbent material of sufficient wet strength and absorbency to hold an effective amount of the sanitizing formulation of the present invention. For example, the wiper can include a nonwoven fabric, woven fabric, knit fabric, wet-strength paper, or combinations thereof. Materials and processes suitable for forming such wiper are well known to those skilled in the art.

For instance, some examples of nonwoven fabrics that may used in the present invention include, but are not limited to, spunbonded webs (apertured or non-apertured), meltblown webs, bonded carded webs, air-laid webs, coform webs, hydraulically entangled webs, and the like. In addition, nonwoven fabrics can contain synthetic fibers (e.g., polyethylenes, polypropylenes, polyvinyl chlorides, polyvinylidene chlorides, polystyrenes, polyesters, polyamides, polyimides, etc.); cellulosic fibers (softwood pulp, hardwood pulp, thermomechanical pulp, etc.); or combinations thereof.

If desired, the nonwoven fabric may also be bonded using techniques well known in the art to improve the durability, strength, hand, aesthetics, texture, and/or other properties of the fabric. For instance, the nonwoven fabric can be thermally (e.g., pattern bonded), ultrasonically, adhesively and/or mechanically (e.g., through-air dried) bonded. For instance, various pattern bonding techniques are described in U.S. Pat. No. 3,855,046 to Hansen; U.S. Pat. No. 5,620,779 to Levy, et al.; U.S. Pat. No. 5,962,112 to Haynes, et al.; U.S. Pat. No. 6,093,665 to Sayovitz, et al.; U.S. Design Pat. No. 428,267 to Romano, et al.; and U.S. Design Pat. No. 390,708 to Brown, which are incorporated herein in their entirety by reference thereto for all purposes.

The nonwoven fabric can be bonded by continuous seams or patterns. As additional examples, the nonwoven fabric can be bonded along the periphery of the sheet or simply across the width or cross-direction (CD) of the web adjacent the edges. Other bond techniques, such as a combination of thermal bonding and latex impregnation, may also be used. Alternatively and/or additionally, a resin, latex or adhesive may be applied to the nonwoven fabric by, for example, spraying or printing, and dried to provide the desired bonding. Still other suitable bonding techniques may be described in U.S. Pat. No. 5,284,703 to Everhart, et al., U.S. Pat. No. 6,103,061 to Anderson, et al., and U.S. Pat. No. 6,197,404 to Varona, which are incorporated herein in its entirety by reference thereto for all purposes.

In one embodiment of the present invention, the wiper is formed from a hydroentangled nonwoven fabric. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

In another embodiment, the wiper is formed from a spunbonded web containing monocomponent and/or multicomponent fibers. Multicomponent fibers are fibers that have been formed from at least two polymer components. Such fibers are usually extruded from separate extruders but spun together to form one fiber. The polymers of the respective components are usually different from each other although multicomponent fibers may include separate components of similar or identical polymeric materials. The individual components are typically arranged in substantially constantly positioned distinct zones across the cross-section of the fiber and extend substantially along the entire length of the fiber. The configuration of such fibers may be, for example, a side-by-side arrangement, a pie arrangement, or any other arrangement.

Multicomponent fibers and methods of making the same are taught in U.S. Pat. No. 5,108,820 to Kaneko, et al., U.S. Pat. No. 4,795,668 to Kruege, et al., U.S. Pat. No. 5,162,074 to Hills, U.S. Pat. No. 5,277,976 to Hogle, et al., U.S. Pat. No. 5,336,552 to Strack, et al., U.S. Pat. No. 5,466,410 to Hills, U.S. Pat. No. 5,069,970 to Largman, et al., U.S. Pat. No. 5,057,368 to Largman, et al., U.S. Pat. No. 5,382,400 to Pike, et al., and U.S. Pat. No. 5,989,004 to Cook, which are incorporated herein in their entirety by reference thereto for all purposes.

When utilized, multicomponent fibers can also be splittable. In fabricating multicomponent fibers that are splittable, the individual segments that collectively form the unitary multicomponent fiber are contiguous along the longitudinal direction of the multicomponent fiber in a manner such that one or more segments form part of the outer surface of the unitary multicomponent fiber. In other words, one or more segments are exposed along the outer perimeter of the multicomponent fiber. For example, splittable multicomponent fibers and methods for making such fibers are described in U.S. Pat. No. 5,935,883 to Pike and U.S. Pat. No. 6,200,669 to Marmon, et al., which are incorporated herein in their entirety by reference thereto for all purposes.

The wiper can also contain a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

In addition, the wiper can also be formed from a material that is imparted with texture one or more surfaces. For instances, in some embodiments, the wiper can be formed from a dual-textured spunbond or meltblown material, such as described in U.S. Pat. No. 4,659,609 to Lamers, et al. and U.S. Pat. No. 4,833,003 to Win, et al., which are incorporated herein in their entirety by reference thereto for all purposes.

Regardless of the materials or processes utilized to form the wiper, it is typically desired that the basis weight of the wiper be from about 20 to about 200 grams per square meter (gsm), and in some embodiments, between about 35 to about 100 gsm. Lower basis weight products may be particularly well suited for use as light duty wipers, while higher basis weight products may be better adapted for use as industrial wipers Because many of the wipers described above utilize non-woven fabrics prepared from inherently hydrophobic (i.e., non-wettable) materials, it is often desired that the surface(s) of the fabrics be rendered more hydrophilic (i.e., wettable) so that the sanitizing formulation can be more readily absorbed by the wiper. For instance, the wiper may be sprayed or coated with a surfactant solution during or after its formation. Once the wiper dries, the surfactant remains thereon until exposure to the sanitizing formulation. Alternatively, a surfactant can be included in the fibrous or polymeric material of the substrate. By containing a surfactant, the resulting wiper can become more wettable so that the aqueous sanitizing formulation is more easily absorbed by the wiper. It should be understood, however, that other well-known methods for increasing the wettability of a surface can also be used in the present invention. For instance, various methods for enhancing the wettability of a fabric are described in U.S. Pat. No. 5,057,361 to Sayovitz, et al., which is incorporated herein in its entirety by reference thereto for all purposes.

The wiper may be applied with a sanitizing formulation, which is described in more detail below, by any suitable method known in the art, such as spraying, dipping, saturating, impregnating, brush coating and the like. The amount of the sanitizing formulation that may be added to the wiper may vary depending upon the type of wiper material utilized, the type of container used to store the wipers, the nature of the sanitizing formulation, and the desired end use of the wipers. Generally, each wiper contains from about 150 to about 600 weight percent and desirably from about 300 to about 500 weight percent of the sanitizing formulation based on the dry weight of the wiper. In embodiments in which the wiper is made from a relatively absorbent substrate (e.g., fabrics containing pulp fibers), the amount of the sanitizing formulation contained within the wiper can be from about 300 to about 600 weight percent and desirably about 500 weight percent based on the dry weight of the wiper. In embodiments in which the wiper is made from a relatively non-absorbent substrate (e.g., polypropylene meltblown or spunbonded fabric), the amount of the sanitizing formulation contained within the wiper can be from about 150 to about 500 weight percent and desirably about 400 weight percent based on the dry weight of the wiper.

II. Sanitizing Formulation

In general, the sanitizing formulation of the present invention, can be used to disinfect and/or sanitize any surface (e.g., food service counters, tables, etc.). As discussed above, the wiper is often formed from a material that is wettable or made wettable by the addition of a surfactant or other compound. For example, in some embodiments, the wiper is from a nonwoven fabric that contains cellulosic fibers (e.g., hydroentangled composite fabric). Certain antimicrobial agents, such as quaternary ammonium compounds, are often readily adsorbed by polar materials. When such antimicrobial agents are adsorbed, they tend to become bound to the polar fibers and are generally less effective in killing bacteria present on a wiping surface.

In accordance with the present invention, it has been discovered that the adsorption of the antimicrobial agent can be controlled by forming the sanitizing formulation from selective components in certain relative amounts. As a result, the adsorption of the antimicrobial agent can be controlled so that at least some or all of the antimicrobial agent remains unbound and thus free to interact with bacteria present on a wiping surface. Moreover, by maximizing the antimicrobial efficacy of the antimicrobial agent in this manner, it has also been discovered that relatively small antimicrobial concentrations can be utilized, while still achieving the desired antimicrobial kill.

Further, because the antimicrobial agent may be utilized in such relatively small amounts and still achieve the desired antimicrobial efficacy, it has also been discovered that the wiper of the present invention may be particularly effective when used in food service environments. For instance, in food service environments, it is typically desired that the amount of antimicrobial agent released from the wiper during use be relatively small in order to minimize the likelihood that the antimicrobial agent will become present in large amounts in food that later contacts the wiped surface. Although the amount of antimicrobial agent released from the wiper in the present invention may vary depending on the nature of the antimicrobial agent and/or other formulation components, the antimicrobial agent is typically present in an amount less than about 2000 parts per million (ppm) of the sanitizing solution released from the wiper. In some embodiments, for example, a quaternary ammonium halide antimicrobial agent, as described in more detail below, can be present in the released sanitizing solution in an amount less than about 400 ppm, and in some embodiments between about 150 ppm to about 400 ppm of the released solution. Again, even when present in the released sanitizing solution in such small amounts, the desired level of antimicrobial efficacy can still be achieved.

In order to provide the aforementioned benefits, the sanitizing formulation of the present invention may contain one or more of the following components:

A. Antimicrobial Agent

In accordance with the present invention, the sanitizing solution applied to the wiper generally includes an antimicrobial agent. Any antimicrobial agent that is capable of inhibiting the growth of gram negative and/or positive bacteria can be utilized in the present invention. In one particular embodiment, the antimicrobial agent includes a quaternary ammonium compound having the following formula:

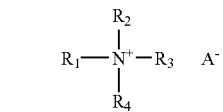

wherein, $R_1$, $R_2$, $R_3$, and $R_4$ are independently selected from the group consisting of H, $C_1$-$C_{30}$ alkyl, $C_1$-$C_{30}$ alkenyl, $C_{1-30}$ alkylethoxy, $C_{1-30}$ alkylphenolethoxy, and the like; and A is selected from the group consisting of halogens (e.g., chlorine, bromine, fluorine, etc.); methosulfates, phosphates, and the like.

For instance, some suitable quaternary ammonium compounds that may be used in present invention include, but are not limited to, benzalkonium chloride (BZK) or other benzalkonium halides, benzethonium chloride or other benzethonium halides, cetylpyridinium chloride, dequalinium chloride, N-myristyl-N-methyl-morpholinium methyl sulfate, poly-N-3-(dimethylammonio)propyl-N-3-(ethyleneoxyethelene dimethylammonio)propylurea dichloride, alpha-4-1-tris(2-hydroxyethyl)ammonium chloride-2-butenyl-omega-tris(2-hydroxyethyl)ammonium chloride, polyoxyethylene (dimethyliminio)ethylene(dimethyliminio)-ethylene dichloride.

In some embodiments, quaternary ammonium halide compounds having the following formula are utilized:

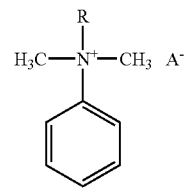

wherein,

R is a $C_8$-$C_{18}$ alkyl group; and

A is a halogen atom, such as chlorine, bromine, fluorine, and the like.

One commercially available example of an antimicrobial agent that includes such a quaternary ammonium compound is available under the trade name BARDAC® 208M from Lonza, Inc., Fairlawn, N.J. Specifically, BARDAC® 208M contains a blend of alkyl dimethyl benzyl ammonium chlorides. Other commercially available examples of suitable quaternary ammonium compounds are believed to include BARDAC® 2050 and BARDAC® 2080 (based on dialkyl ($C_8$-$C_{10}$)dimethyl ammonium chloride); BARDAC® 2250 and BARDAC® 2280 (didecyl dimethyl ammonium chloride); BARDAC® LF and BARDAC® LF 80 (based on dioctyl dimethyl ammonium chloride); BARQUAT® MB-50 and BARQUAT® MB-80 (based on alkyl dimethyl benzyl ammonium chloride); BARQUAT® MX-50 and BARQUAT® MX-80 (based on alkyl dimethyl benzyl ammonium chloride); BARQUAT® OJ-50 and BARQUAT® OJ-80 (based on alkyl dimethyl benzyl ammonium chloride); BARQUAT® 4250, BARQUAT® 4280, BARQUAT® 4250Z, and BARQUAT® 4280Z (based on alkyl dimethyl benzyl ammonium chloride and/or alkyl dimethyl ethyl benzyl ammonium chloride); and BARQUAT® MS-100 (based on myristyl dimethyl benzyl ammonium chloride), which are available from Lonza, Inc., Fairlawn, N.J.

In addition to quaternary ammonium compounds, other antimicrobial agents may also be utilized in the present invention. For instance, some suitable antimicrobial agents that may be utilized include, but are not limited to, halogenated diphenyl ethers like 2,4,4'-trichloro-2'-hydroxy-diphenyl ether (Triclosan® or TCS) or 2,2'-dihydroxy-5,5'-dibromo-diphenyl ether; phenolic compounds like phenoxyethanol, phenoxy propanol, phenoxyisopropanol, para-chloro-meta-xylenol (PCMX), etc.; bisphenolic compounds like 2,2'-methylene bis(4-chlorophenol), 2,2'-methylene bis(3,4,6-trichlorophenol), 2,2'-methylene bis(4-chloro-6-bromophenol), bis(2-hydroxy-3,5-dichlorophenyl) sulphide, and bis(2-hydroxy-5-chlorobenzyl)sulphide; halogenated carbanilides (e.g., 3,4,4'-trichlorocarbanilides (Triclocarban® or TCC); benzyl alcohols; chlorhexidine; chlorhexidine gluconate; and chlorhexidine hydrochloride; Other suitable antimicrobial agents are described in WO 96/06152; WO/9606153; and U.S. Pat. No. 6,201,695 to Beerse, et al., which are incorporated herein in their entirety by reference thereto for all purposes. In addition, various other antimicrobial agents are set forth in Title 21, Section 178.010. of the United States Code of Federal Regulations (C.F.R.).

The amount of the antimicrobial agent utilized in the sanitizing formulation can generally vary depending on the relative amounts of the other components present within the formulation. Typically, the antimicrobial agent is present in the formulation in an amount between about 0.01% to about 1% by weight, in some embodiments between about 0.01% to about 0.4% by weight, and in some embodiments, between about 0.1% to about 0.4% by weight of the disinfectant formulation.

B. Sequestrant

In addition to an antimicrobial agent, the sanitizing formulation of the present invention can also contain a sequestrant. A sequestrant is a substance whose molecules can form one or more bonds with a metal ion. In particular, water often contains metal ions, such as calcium ions, that might react with anionic components (e.g., surfactants, acids, etc.) present within the sanitizing formulation. Without being limited by theory, it is believed that a sequestrant can form a complex with such metal ions so that the remaining anionic components are capable of fulfilling their desired function. For example, in one embodiment, a surfactant that remains substantially unreacted with metal ions can better function as a cleansing agent. Moreover, in some instances, it is also believed that the sequestrant can further improve the ability of the sanitizing formulation to inhibit the growth of gram negative and/or gram positive bacteria.

Some examples of sequestrants that may be used in the sanitizing formulation of the present invention include, but are not limited to, ethylenediamines, ethylenediaminetetraacetic acids (EDTA) acid and/or salts thereof, citric acids and/or salts thereof, glucuronic acids and/or salts thereof, polyphosphates, organophosphates, dimercaprols, and the like.

The amount of the sequestrant utilized in the sanitizing formulation can generally vary depending on the relative amounts of the other components present within the formulation. Typically, when utilized, the sequestrant is present in the formulation in an amount between about 0.01% to about 5% by weight, in some embodiments between about 0.01 to about 1.5% by weight, and in some embodiments, between about 0.1% to about 1% by weight of the sanitizing formulation.

C. Surfactant

Besides the above-mentioned components, the sanitizing formulation of the present invention may also include at least one surfactant. Surfactants can provide a number of benefits to the resulting sanitizing formulation. For instance, when utilizing a substrate that is generally nonpolar, surfactants can increase the wettability of the substrate, thereby allowing the sanitizing formulation to be absorbed by the substrate. Moreover, the surfactant can also improve the ability of the sanitizing formulation to clean surfaces. In some instances, the surfactant may also help to dissolve ingredients present within the formulation, such as certain types of antimicrobial agents.

Nonionic, anionic, cationic, and amphoteric surfactants may all be suitable for use in the present invention. For example, in some embodiments, such as when the disinfectant formulation contains a quaternary ammonium antimicrobial agent, it may be desired to utilize one or more nonionic surfactants. Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, and mixtures thereof.

Various specific examples of suitable nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Additional nonionic surfactants that can be used include water soluble alcohol ethylene oxide condensates are the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name Tergitol® from Union Carbide Corp., Danbury, Conn. Specific examples of such commercially available nonionic surfactants of the foregoing type are $C_{11}$-$C_{15}$ secondary alkanols condensed with either 9 moles of ethylene oxide (Tergitol® 15-S-9) or 12 moles of ethylene oxide (Tergitol® 15-S-12) marketed by Union Carbide Corp., (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include Igepal® CO-630 (a nonyl phenol ethoxylate) marketed by ISP Corp. (Wayne, N.J.). Suitable non-ionic ethoxylated octyl and nonyl phenols include those having from about 7 to about 13 ethoxy units. Such compounds are commercially available under the trade name Triton® X (Union Carbide, Danbury Conn.).

Alkyl polyglycosides may also be used as a nonionic surfactant in the present inventive compositions. Suitable alkyl polyglycosides are known nonionic surfactants that are alkaline and electrolyte stable. Alkyl mono and polyglycosides are prepared generally by reacting a monosaccharide, or a compound hydrolyzable to a monosaccharide with an alcohol such as a fatty alcohol in an acid medium.

One example of such alkyl polyglycosides is APG™ 325 CS GLYCOSIDE, which is described as being a 50% $C_9$-$C_{11}$ alkyl polyglycoside, also commonly referred to as D-glucopyranoside. Another example of an alkyl polyglycoside surfactant is GLUCOPON™ 625 CS, which is described as being a 50% $C_{10}$-$C_{16}$ alkyl polyglycoside, also commonly referred to as a D-glucopyranoside. Both APG™ 325 CS GLYCOSIDE and GLUCOPON™ 625 CS are commercially available from Henkel Corp., Ambler Pa.

Other useful nonionic surfactants include compositions based on amine oxides. One general class of useful amine oxides include alkyl di(lower alkyl) amine oxides in which the alkyl group has about 10-20, and preferably 12-16 carbon atoms, and can be straight or branched chain, saturated or unsaturated. The lower alkyl groups include between 1 and 7 carbon atoms. Examples include lauryl, dimethyl amine oxide, myristyl dimethyl amine oxide, and those in which the alkyl group is a mixture of different amine oxide, dimethyl cocoamine oxide, dimethyl (hydrogenated tallow) amine oxide, and myristyl/palmityl dimethyl amine oxide.

Another class of useful amine oxides include alkyl di(hydroxy lower alkyl) amine oxides in which the alkyl group has about 10-20, and particularly 12-16 carbon atoms, and can be straight or branched chain, saturated or unsaturated. Examples are bis(2-hydroxyethyl) cocoamine oxide, bis(2-hydroxyethyl) tallow amine oxide, and bis(2-hydroxyethyl) stearylamine oxide. Moreover, still other useful amine oxides include those characterized as alkylamidopropyl di(lower alkyl) amine oxides, in which the alkyl group has about 10-20 carbon atoms, and can be straight or branched chain, saturated or unsaturated. Examples are cocoamidopropyl dimethyl amine oxide and tallowamidopropyl dimethyl amine oxide.

Additional useful amine oxides include alkylmorpholine oxides in which the alkyl group has about 10-20 carbon atoms, and can be straight or branched chain, saturated or unsaturated. Further examples of amine oxides include those that commercially under the trade name AMMONYX (Stepan Co., Chicago Ill.).

In addition to nonionic surfactants, the sanitizing formulation may also other types of surfactants. For instance, in some embodiments, amphoteric surfactants may also be used. For instance, one class of amphoteric surfactants that may be used in the present invention are derivatives of secondary and tertiary amines having aliphatic radicals that are straight chain or branched, wherein one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

Additional classes of suitable amphoteric surfactants include phosphobetaines and the phosphitaines. For instance, some examples of such amphoteric surfactants include, but are not limited to, sodium coconut N-methyl taurate, sodium oleyl N-methyl taurate, sodium tall oil acid N-methyl taurate, sodium palmitoyl N-methyl taurate, cocodimethylcarboxymethylbetaine, laurydimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)propylsultaine, di-sodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocoamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

In certain instances, it may also be desired to utilize one or more anionic surfactants within the sanitizing formulation. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$-$C_{18}$ alkyl sulfates, $C_8$-$C_{18}$ fatty acid salts, $C_8$-$C_{18}$ alkyl ether sulfates having one or two moles of ethoxylation, $C_8$-$C_{18}$ alkamine oxides, $C_8$-$C_{18}$ alkoyl sarcosinates, $C_8$-$C_{18}$ sulfoacetates, $C_8$-$C_{18}$ sulfosuccinates, $C_8$-$C_{18}$ alkyl diphenyl oxide disulfonates, $C_8$-$C_{18}$ alkyl carbonates, $C_8$-$C_{18}$ alpha-olefin sulfonates, methyl ester sulfonates, and blends thereof. The $C_8$-$C_{18}$ alkyl group can be straight chain (e.g., lauryl) or branched (e.g., 2-ethylhexyl). The cation of the anionic surfactant can be an alkali metal (e.g., sodium or potassium), ammonium, $C_1$-$C_4$ alkylammonium (e.g., mono-, di-, tri), or $C_1$-$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and similar surfactants.

Cationic surfactants, such as cetylpyridinium chloride and methylbenzethonium chloride, may also be utilized.

The amount of surfactant utilized in the sanitizing formulation can generally vary depending on the relative amounts of the other components present within the formulation. When utilized, the surfactant can be present in the formulation in an amount between about 0.01% to about 5% by weight, in some embodiments between about 0.01% to about 2% by weight, and in some embodiments, between about 0.01% to about 1% by weight of the sanitizing formulation. Although any surfactant may generally be utilized, the sanitizing formulation of the present invention often contains at least one nonionic surfactant. For example, the nonionic surfactant can be present in the formulation in an amount between about 0.01% to about 1% by weight, in some embodiments between about 0.01% to about 0.5% by weight, and in some embodiments, between about 0.01% to about 0.1% by weight of the sanitizing formulation.

D. Non-Aqueous Solvent

In some instances, the sanitizing formulation of the present invention may also include one or more non-aqueous solvents. Although not required, non-aqueous solvents can sometimes aid in dissolving certain components (e.g., preservatives, antimicrobial agent, etc.) of the sanitizing formulation. Moreover, in some instances, the non-aqueous solvent may also enhance the antimicrobial efficacy of the sanitizing formulation. Examples of some suitable non-aqueous solvents include, but are not limited to, glycols, such as propylene glycol, butylene glycol, triethylene glycol, hexylene glycol, polyethylene glycols, ethoxydiglycol, and dipropyleneglycol; alcohols, such as ethanol, n-propanol, and isopropanol; triglycerides; ethyl acetate; acetone; triacetin; and combinations thereof. Especially desired solvent combinations include a glycol, particularly hexylene and/or propylene glycol, and one or more lower alcohols, particularly isopropanol, n-propanol, and/or ethanol.

The amount of solvent utilized in the sanitizing formulation can generally vary depending on the relative amounts of the other components present within the formulation. When utilized, the solvent is typically present in the formulation in an amount between about 0.001% to about 30% by weight, in some embodiments between about 1 to about 15% by weight, and in some embodiments, between about 5% to about 15% by weight of the sanitizing formulation. For example, in some embodiments, the solvent contains a glycol (e.g., propylene glycol) and alcohol (e.g., ethanol) such that the glycol is present in an amount of between about 0.001% to about 10% by weight of the sanitizing formulation and the alcohol is present in an amount of between about 0.001 to about 5% by weight of the sanitizing formulation.

E. Preservatives

In some embodiments, the sanitizing formulation can also contain one or more preservatives. Although not required, preservatives can inhibit the growth of microorganisms on the premoistened wiper.

Some suitable preservatives that can be used in the present invention include, but are not limited to, Kathon CG®, which is a mixture of methylchloroisothiazolinone and methylisothiazolinone available from Rohm & Haas; Mackstat H 66 (available from McIntyre Group, Chicago, Ill.); DMDM hydantoin (e.g., Glydant Plus, Lonza, Inc., Fair Lawn, N.J.); iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; amidazolidinyl urea; diazolidinyl urea; and the like. Other suitable preservatives include those sold by Sutton Labs, such as "Germall 115" (amidazolidinyl urea), "Germall II" (diazolidinyl urea), and "Germall Plus" (diazolidinyl urea and iodopropynyl butylcarbonate).

When utilized, the amount of the preservative utilized in the sanitizing formulation can generally vary depending on the relative amounts of the other components present within the formulation. For example, in some embodiments, the preservative is present in the formulation in an amount between about 0.001% to about 5% by weight, in some embodiments between about 0.001 to about 1% by weight, and in some embodiments, between about 0.1% to about 0.15% by weight of the disinfectant formulation.

F. pH Modifiers

In general, the pH of the sanitizing formulation may be controlled to be within any desired range. For instance, certain antimicrobial agents and/or other components may be more effective at a lower pH, while other antimicrobial agents and/or other components may be more effective at a higher pH. For instance, when the antimicrobial agent contains quaternary ammonium compound(s), it is typically desired that the pH be maintained at a relatively high level, i.e., greater than about 6, in some embodiments greater than about 8, and in some embodiments, between about 9 to about 12. Such relatively high pH levels can improve the efficacy of many quaternary ammonium antimicrobial agents in killing gram negative and/or positive bacteria.

If necessary, various pH modifiers may be utilized in the disinfectant formulation to achieve the desired pH level. For instance, some examples of basic pH modifiers that may be used in the present invention include, but are not limited to, ammonia; mono-, di-, and tri-alkyl amines; mono-, di-, and tri-alkanolamines; alkali metal and alkaline earth metal hydroxides; alkali metal and alkaline earth metal silicates; and mixtures thereof. Specific examples of basic pH modifiers are ammonia; sodium, potassium, and lithium hydroxide; sodium, potassium, and lithium meta silicates; monoethanolamine; triethylamine; isopropanolamine; diethanolamine; and triethanolamine.

Moreover, some examples of acidic pH modifiers that may be used in the present invention include, but are not limited to, mineral acids; and carboxylic acids; and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, maleic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), cross-linked polyacrylic acids having a molecular weight of less than about 250,000, poly (methacrylic) acid, and naturally occurring polymeric acids such as carageenic acid, carboxymethyl cellulose, and alginic acid.

When utilized, the amount of the pH modifier can be present in any effective amount needed to achieve the desired pH level. For example, in some embodiments, the pH modifier is present in the formulation in an amount between about 0.001% to about 5% by weight, in some embodiments between about 0.001 to about 5% by weight, and in some embodiments, between about 0.1% to about 0.25% by weight of the sanitizing formulation. In particular embodiments, the pH modifier contains an alkali metal silicate (e.g., sodium meta silicate) and an alkali metal hydroxide (e.g., sodium hydroxide) such that the silicate is present in an amount of between about 0.001% to about 0.2% by weight of the sanitizing formulation and the hydroxide is present in an amount of between about 0.001 to about 0.05% by weight of the sanitizing formulation.

G. Carrier

It is usually desired that water be utilized as the carrier of the sanitizing formulation, although it should be understood that other suitable carriers are also contemplated in the present invention. Typically, water is present in the sanitizing formulation in an amount between about 1% to about 99% by weight, and in some embodiments, between about 60% to about 99% by weight of the sanitizing formulation.

H. Other Optional Ingredients

In order to better enhance the benefits to consumers, other optional ingredients can also be used. For instance, some classes of ingredients that can be used include, but are not limited to: antioxidants (product integrity); anti-reddening agents, such as aloe extract; astringents—cosmetic (induce a tightening or tingling sensation on skin); astringents—drug (a drug product which checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); external analgesics (a topically applied drug that has a topical analgesic, anesthetic, or antipruritic effect by depressing cutaneous sensory receptors, of that has a topical counterirritant effect by stimulating cutaneous sensory receptors); film formers (to hold active ingredients on the skin by producing a continuous film on skin upon drying); fragrances (consumer appeal); hydrotropes (helps dissolve some antimicrobial agents); opacifiers (reduce the clarity or transparent appearance of the product); skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); sunscreens (ingredients that absorb at least 85 percent of the light in the UV range at wavelengths from 290 to 320 nanometers, but transmit UV light at wavelengths longer than 320 nanometers); and thickeners (to increase the viscosity of the formulation).

III. Delivery System

In one embodiment, the wipers are provided in a continuous, perforated roll. Perforations provide a line of weakness by which the wipers can be more easily separated. For instance, in one embodiment, a 6" high roll contains 12" wide wipers that are v-folded. The roll is perforated every 12 inches to form 12"×12" wipers. In another embodiment, the wipers are provided as a stack of individual wipers. Regardless of the manner in which the wipers are provided, the sanitizing formulation can, in some embodiments, be added to the container. In one embodiment, for example, the sanitizing formulation is added to the container in such an amount that it comprises 475% of the weight of a single 12"×12" wiper.

It is envisioned that the wipers are inserted on end in a selectively resealable container (e.g., cylindrical). Some examples of suitable containers include rigid tubs, film pouches, etc. One particular example of a suitable container for holding the wipers is a rigid, cylindrical tub (e.g., made from polyethylene) that is fitted with a re-sealable air-tight lid (e.g., made from polypropylene) on the top portion of the container. The lid has a hinged cap initially covering an opening positioned beneath the cap. The opening allows for the passage of wipers from the interior of the sealed container whereby individual wipers can be removed by grasping the wiper and tearing the seam off each roll. The opening in the lid is appropriately sized to provide sufficient pressure to remove any excess liquid from each wiper as it is removed from the container.

When removed from the container, the wiper contains a sufficient amount of sanitizing formulation to disinfectant or sanitize a surface. As the wiper is rubbed on the surface, it releases the sanitizing formulation, which contacts bacteria present thereon. The wiper can also provide an abrasive action and a reabsorption capability to remove contaminants from the surface. After use, the wiper can be disposed. The sanitizing formulation may remain on the surface to help kill or inhibit the growth of bacteria thereon for a certain period of time.

Other suitable wiper dispensers, containers, and systems for delivering wipers are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

IV. Antimicrobial Efficacy

The sanitizing formulation of the present invention is generally capable of inhibiting the growth of a wide variety of microbes. Specifically, it has been discovered that the sanitizing formulation is particularly effective in killing gram negative and/or gram positive bacteria when contacted therewith. The table below lists several types of gram negative and gram positive bacteria that may be effectively killed by the disinfectant formulation of the present invention. The table includes the name of the bacteria, the ATCC (American Type Culture Collection) identification number, and the abbreviation for the name of the organism used hereafter.

| Organism | ATCC # | Abbreviation | Gram Type |
|---|---|---|---|
| Staphylococcus aureus | 6538 | S. aureus | positive |
| Escherichia coli | 11229 | E. coli | negative |
| Klebsiella pneumoniae | 10031 | K. pneum. | negative |
| Salmonella choleraesuis | 10708 | S. choler. | negative |

For example, it has been determined that the sanitizing formulation of the present invention can provide a log reduction for S. aureus (gram positive) and/or E. coli (gram negative) of at least about 2, in some embodiments at least about 3, in some embodiments at least about 4, and in some embodiments, at least about 5 (e.g., about 6). Log reduction, for example, can be determined from the % bacteria population killed by the formulation according to the following correlations:

| % Reduction | Log Reduction |
|---|---|
| 90 | 1 |
| 99 | 2 |
| 99.9 | 3 |
| 99.99 | 4 |
| 99.999 | 5 |
| 99.9999 | 6 |

% bacteria reduction is determined according to the Germicidal and Detergent Sanitizing Action of Disinfectants Method as described in Chapter 6, Disinfectants, *Official Methods of Analysis of AOAC International*, 16$^{th}$ Edition, 1995 Section 6.3.03. In particular, the values of % bacteria reduction set forth herein were determined according to the above-referenced Test Method with the following procedural modifications:

1. Test Conditions

Wipers having a size of 6"×8", 10"×12", or 12"×12" are initially selected. The wipers are impregnated with the desired amount of sanitizing formulation and formed into a roll. Two wiper sheets are removed from the roll and discarded. A third wiper sheet is then removed for testing. The third wiper is then used to wipe a certain number of carriers (e.g., flat panels, dishes, etc.), which can vary as well known to those skilled in the art. For instance, 4 carriers can be used. One wipe is used to wipe the specified total test surface area represented by wiping consecutive carriers. The total surface area wiped varies depending on the size of the carrier, which can be selected from carrier sizes of 3"×6", 4.5"×8", or 10.3"×14".

Thus, for example, when the carrier size is 10.3"×14", the surface area wiped per carrier measures approximately 10.3"×14", allowing each carrier to represent 1 square foot of wiped test surface (4 carriers represent 4 square feet of total surface area wiped). The wiper is folded two times in half so that each separate folded portion of the wiper wipes 1 consecutive carrier for the 4 carriers.

Exposure conditions are for 30 seconds at 23±1° C. after a wiping time of 30 seconds.

The neutralizer utilized is the AOAC Neutralizer Blanks with Sea Sand in 400-mL amounts. The neutralizer is added to the carrier and then the surface is rubbed [~34 times in the vertical position, ~18 times in the horizontal position, and once around the entire edge (repeat 2 times) in a period of approximately 1 minute] with a sterile rubber policeman to remove the bacteria.

Other modifications to the AOAC method are as follows:

1) The tested organism is harvested using 1.5 mL of AOAC Phosphate Buffer Dilution Water per bottle instead of 3.0 mL as listed in Section 6.3.03D of the AOAC method.

2) A 0.8-mL aliquot of the adjusted test culture suspension (~1.5±0.5×10$^8$) is used to inoculate each test surface so that each area of test surface (1 carrier/1 square foot) is inoculated to contain approximately 2.8×10$^7$ CFU/carrier for 1 carrier [1 sq. ft.] yielding a count of ~7.5–12.5×10$^7$ CFU/total surface area [4 sq. ft.]. The inoculum is spread evenly over the test piece with the aid of an inoculating loop and then the carrier will be allowed to air dry for 40 min at 37±2° C. and a relative humidity of at least 50%. The carriers are loosely covered with aluminum foil during the drying process. Four carriers are inoculated for each treatment and contact time and four carriers will be inoculated for the numbers control.

3) Growth is confirmed by macroscopic examination rather than the method listed in Section 6.3.03J of the AOAC method.

4) The recovery medium is Tryptone Glucose Extract Agar with 25 mL/L AOAC Stock Neutralizer. Incubation is at 35±2° C. for 48±2 hours. Plating is conducted within thirty minutes of neutralizing the test substance by the Pour Plate Method. Two, 10-mL amounts (10$^{-1}$) of the AOAC Neutralizer Blanks with Sea Sand are plated across three plates and duplicate 1-mL and 0.1-mL amounts (10$^{-2}$ and 10$^{-3}$ dilutions) are pour plated. [AOAC Phosphate Buffer Dilution Water with Sear Sand (400-mL) and AOAC Phosphate Buffer Dilution Water (9-mL) and Tryptone Glucose Extract Agar will be used for the numbers controls.]. Plate counts are conducted in duplicate (a+b) and averaged for each carrier. Colony counts per milliliter are multiplied by 4 to yield Colony forming Units (CFU's) per square foot.

2. Test Observations

Plate counts are conducted on the expressed fluid from the wipers immediately after wiping all 4 of the carriers. Dilutions are conducted in 9.9 mL or 9.0 mL volumes of AOAC Neutralizer Blanks with plating as outlined in Section 13.6 (4 with modifications to account for use of 100 mL of diluent in place of 400 mL of diluent.

The percent reduction in numbers of test bacteria per total square foot of surface area tested (each carrier) is determined as follows:

$$\% \text{ Reduction/number of sq. ft. tested} = \frac{\frac{[\text{Sum of Numbers Control (Carriers } 1a + 1b + \ldots xa + xb)]}{2} - \frac{[\text{Sum of Survivors of Individual Carriers (Carriers } 1a + 1b \ldots + xa + xb)]}{2}}{\frac{[\text{Sum of Numbers Control (Carriers } 1a + 1b + \ldots xa + xb)]}{2}} \times 100$$

wherein, x represents the total number of carriers utilized.

It should be understood that the testing conditions, parameters, or equipment set forth above can be modified if desired. It should be understood that such modifications are contemplated by the present invention, and thus the present invention is not limited to any particular testing conditions, parameters, or equipment used in determining antimicrobial kill efficacy.

VI. Antimicrobial Kill Efficiency Ratio (KER)

As discussed above, it has been discovered that the selection and relative amounts of the components of the sanitizing formulation can be carefully controlled so that the desired antimicrobial kill can be achieved at relatively small amounts of antimicrobial agents. This phenomenon can be quantified by the "Kill Efficiency Ratio" (KER). The Kill Efficiency Ratio is the number of bacteria killed divided by the parts per million of the antimicrobial agent added to the original sanitizing formulation. A relatively high Kill Efficiency Ratio, for example, indicates good antimicrobial efficacy at low concentrations of antimicrobial agent. Specifically, the Kill Efficiency Ratio (KER) is determined according to the following equation:

$$KER = \frac{[\text{number of bacteria killed}/1000]}{\text{ppm of antimicrobial agent in the sanitizing formulation}}$$

The number of bacteria killed (per total square foot of surface area tested for each carrier) is determined as follows:

$$\text{\# Killed/number of sq. ft.} = \frac{[\text{Sum of Numbers Control}(\text{Carriers } 1a + 1b + \ldots xa + xb)]}{2} - \frac{[\text{Sum of Survivors of Individual }(\text{Carriers } 1a + 1b + \ldots xa + xb)]}{2}$$

In most embodiments of the present invention, the Kill Efficiency Ratio of the sanitizing formulation is at least about 10, in some embodiments at least about 40, in some embodiments, at least about 100, and in some embodiments, at least about 200.

VII. Antimicrobial Reduction

As discussed above, it has been discovered that the selection and relative amounts of the components of the sanitizing formulation can allow control over the amount of antimicrobial agent absorbed into the wiper and not released during use. This phenomenon can be quantified by Antimicrobial Reduction. In most embodiments of the present invention, the Antimicrobial Reduction is less than about 95%, and in some embodiments, between about 60% to about 80%.

The Antimicrobial Reduction may generally be determined according to the following formula:

$$100 \times [(Q_i - Q_r)/Q_i]$$

wherein, $Q_i$ is the amount of antimicrobial agent added to the sanitizing formulation, and $Q_r$ is the amount of antimicrobial agent released as a solution released from the wiper.

For example, to determine the amount of a benzethonium chloride antimicrobial agent present within a released solution ($Q_r$), the following procedure may be used.

1. REAGENTS (as indicated or equivalent)
   1.1. Sodium Lauryl Sulfate (SLS) Solution, 0.003 N (e.g., 0.864 g per liter reagent water).
   1.2. Sodium Lauryl Sulfate, A.R. Grade
   1.3. Chloroform, A.R. Grade
   1.4. Salt Buffer Solution, pH 10-11 (e.g., 7 g Sodium Carbonate—A.R. Grade, 100 g Sodium Sulfate—A.R. Grade per liter reagent water).
   1.5. Bromophenol Blue Indicator (e.g., 0.1% in 50:50 v/v Ethanol:Water with 0.5 NaOH added dropwise until solution is blue).
   1.6. Benzethonium Chloride, U.S.P. Grade
2. EXPERIMENTAL PROCEDURE
   2.1. Standardization of the Sodium Lauryl Sulfate (SLS) Solution
      a. Dry an aliquot of Benzethonium Chloride (BzCl) in a sealable container in a vacuum oven at 60-62° C. for at least 12 hours prior to the start of testing. Remove the material from the oven, cover and allow it to cool in a dessicator.
      b. Weigh 0.1344 g of the dried Benzethonium Chloride ($Wt_{STD}$) into a 250 ml volumetric flask. Dilute to volume with reagent water and reweigh ($Wt_{SOLUTION}$). Record weights to four decimal places. This solution must be stored in an airtight container.
      c. Weigh 10 g of the Benzethonium Chloride solution ($Wt_{ALIQUOT}$) into a titration flask (250 ml Erlenmeyer flask) and record the weight to two decimal places. Titrate a minimum of 3 aliquots according to section 2.2.
   2.2. SLS Standardization Titration
      a. Add approximately 10.0 ml of chloroform, 5.0 ml of salt buffer solution and 4-5 drops of bromophenol blue indicator solution to the titration flask that already contains the Benzethonium Chloride solution.
      b. Shake the flask vigorously.
      c. Using the digital burette, titrate the Benzethonium Chloride solution with the SLS solution with vigorous shaking between additions of titrant. Allow layers to separate for a few seconds before adding more titrant. The endpoint should be between 4.0 and 5.0 ml. As the endpoint is approached (indicated by the upper layer turning white), titrant additions should be as small as possible. The endpoint is defined as the definite appearance of purple in the upper layer and the disappearance of color (blue) in the bottom layer. Record the volume of titrant required to reach the endpoint to the nearest decimal.
   2.3. Calculate the normality of the SLS standard solution. Use Equation 1 below:

$$N_{NaLSO_4} = \frac{\frac{Wt_{ALIQUOT} \cdot Wt_{STD}}{Wt_{SOLUTION}} \cdot P_{DryBasis} \cdot 10}{448.1 \cdot Vol_{NaLSO_4}} \qquad \text{EQUATION 1}$$

Where:
   $N_{NaLSO4}$=Normality of Sodium lauryl sulfate titrant (N)
   $Wt_{STD}$=Weigh of Benzethonium chloride from 2.1.b
   $Wt_{ALIQUOT}$=Aliquot Weight from 2.1.c
   $Wt_{SOLUTION}$=Total Solution Weight from 2.1.b
   $Vol_{NaLSO4}$=Volume of Sodium lauryl sulfate titrant (ml)
   $P_{DryBasis}$=Purity of Benzethonium chloride (%)
   448.1=Equivalent Weight of BzCl (g/mole)

2.4 Prepare the sample for analysis.
   a. If analyzing SANITIZING SOLUTION ONLY (not expressed from wiper), proceed to step 2.5 a.
   b. If analyzing SANITIZING SOLUTION EXPRESSED FROM WIPER, remove wipers from canister and fill syringe with wipers. Depress syringe to extract the solution from the wiper and collect the solution in a separate beaker. Proceed to step 2.5 a.
2.5 Analyze the samples.
   a. Using a 10 ml volumetric pipet, transfer 10 ml of the test sample into a 250 ml Erlenmeyer flask. NOTE: Certain circumstances may require modification of the sample weight. This may be done at the analyst's discretion.
   b. Add about 10 ml of chloroform, 5 ml of salt buffer solution and 4-5 drops of bromophenol blue indicator solution to the titration flask that contains the test sample. (NOTE: If the test sample is acidic, add NaOH solution dropwise to achieve a pH of 10-11).
   c. Shake the flask vigorously.
   d. Using the digital burette, titrate the test sample solution with the SLS solution with vigorous shaking between additions of titrant. Allow layers to separate for a few seconds before adding more titrant. The endpoint should be between 4.0 and 5.0 ml. As the endpoint is approached (indicated by the upper layer turning white), titrant additions should be as small as possible. The endpoint is defined as the definite appearance of purple in the upper layer and the disappearance of color (blue) in the bottom layer.

2.6 Calculate the results using Equation 2 below:

$$L_{QUAT} = \frac{V_{NaLSO4} \cdot N_{NaLSO4} \cdot 342 \cdot 1000}{V_{SA}} \quad \text{EQUATION 2}$$

Where:

$L_{QUAT}$=Level of Quat in test sample (ppm)

$V_{NaLSO4}$=Volume of sodium lauryl sulfate titrant (ml)

$N_{NaLSO4}$=Normality of sodium lauryl sulfate titrant (N) (from Equation 1)

342=Equivalent Weight of Quat (g/mole)

$V_{SA}$=Volume of Test Sample (ml)

Repeat steps 2.4 and 2.5 for at least two additional test samples (N=3).

It should be understood that the testing conditions, parameters, or equipment set forth above can be modified if desired, particularly when other antimicrobial agents are utilized. Such modifications are contemplated by the present invention, and thus the present invention is not limited to any particular testing conditions, parameters, or equipment used in determining the remaining level of antimicrobial agent in solution.

The present invention may be better understood with reference to the following examples.

EXAMPLE 1

The ability to form a wiper having good antimicrobial efficacy was demonstrated. In particular, a roll of wipers formed from a dual-textured polypropylene meltblown web having a basis weight of 33.9 gsm (available under the trade name Sanituff® from Kimberly-Clark) was initially provided. The wipers were then saturated (by hand) with sanitizing Formulations 1-18 (set forth below) in an amount of 380% by weight of the wiper.

| Component | Active Concentration |
|---|---|
| Formulation# 1 | |
| Benzalkonium Chloride[1] | 400 ppm |
| EDTA[2] | 0.03 wt. % |
| Nonionic Surfactant[3] | 0.50 wt. % |
| Ethanol | 5.00 wt. % |
| Methyl Paraben | 0.10 wt. % |
| Propyl Paraben | 0.04 wt. % |
| Water | To balance |
| Formulation# 2 | |
| Benzalkonium Chloride[1] | 380 ppm |
| EDTA[2] | 0.03 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To balance |
| pH | 6.8 |
| Formulation# 3 | |
| Benzalkonium Chloride[1] | 380 ppm |
| EDTA[2] | 0.30 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To balance |
| pH | 8.3 |
| Formulation# 4 | |
| Benzalkonium Chloride[1] | 380 ppm |
| EDTA[2] | 0.03 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To Balance |
| pH | 6.7 |
| Formulation# 5 | |
| Benzalkonium Chloride[1] | 380 ppm |
| EDTA[2] | 0.03 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Sodium Meta Silicate | 0.07 wt. % |
| Water | To Balance |
| pH | 8.9 |
| Formulation# 6 | |
| Benzalkonium Chloride[1] | 380 ppm |
| EDTA[2] | 0.30 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To Balance |
| pH | 8.0 |
| Formulation# 7 | |
| Benzalkonium Chloride[4] | 190 ppm |
| EDTA[2] | 0.30 wt. % |
| Nonionic Surfactant[3] | 0.50 wt. % |
| Ethanol | 10.0 wt. % |
| Water | To Balance |
| pH | 8.0 |
| Formulation# 8 | |
| Benzalkonium Chloride[1] | 380 ppm |
| EDTA[2] | 1.00 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To Balance |
| Formulation# 9 | |
| Benzalkonium Chloride[1] | 320 ppm |
| EDTA[2] | 0.30 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To Balance |

| Component | Active Concentration |
|---|---|
| Formulation# 10 | |
| Benzalkonium Chloride[1] | 380 ppm |
| EDTA[2] | 1.30 wt. % |
| Nonionic Surfactant[3] | 0.50 wt. % |
| Methyl Paraben | 0.10 wt. % |
| Propyl Paraben | 0.04 wt. % |
| Propylene Glycol | 10.0 wt. % |
| Water | To Balance |
| Formulation# 11 | |
| Benzalkonium Chloride[1] | 380 ppm |
| EDTA[2] | 1.30 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To Balance |
| Formulation# 12 | |
| Benzalkonium Chloride[1] | 380 ppm |
| EDTA[2] | 1.30 wt. % |
| Nonionic Surfactant[3] | 0.50 wt. % |
| Ethanol | 20.0 wt. % |
| Methyl Paraben | 0.10 wt. % |
| Propyl Paraben | 0.04 wt. % |
| Water | To Balance |
| Formulation# 13 | |
| Benzalkonium Chloride[1] | 380 ppm |
| EDTA[2] | 1.30 wt. % |
| Nonionic Surfactant[3] | 0.50 wt. % |
| Ethanol | 30.0 wt. % |
| Methyl Paraben | 0.10 wt. % |
| Propyl Paraben | 0.04 wt. % |
| Water | To Balance |
| Formulation# 14 | |
| Benzalkonium Chloride[1] | 800 ppm |
| EDTA[2] | 1.30 wt. % |
| Nonionic Surfactant[3] | 0.50 wt. % |
| Ethanol | 10.0 wt. % |
| Methyl Paraben | 0.10 wt. % |
| Propyl Paraben | 0.04 wt. % |
| Water | To Balance |
| Formulation# 15 | |
| Benzalkonium Chloride[1] | 380 ppm |
| Nonionic Surfactant[3] | 0.50 wt. % |
| Methyl Paraben | 0.10 wt. % |
| Propyl Paraben | 0.04 wt. % |
| Water | To Balance |
| pH | 9.7 |
| Formulation# 16 | |
| Benzalkonium Chloride[1] | 415 ppm |
| EDTA[2] | 0.70 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To Balance |
| pH | 9.5 |
| Quat Released from Solution | 384 ppm |
| Formulation# 17 | |
| Benzalkonium Chloride[1] | 407 ppm |
| EDTA[2] | 0.45 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To Balance |
| pH | 9.1 |
| Quat Released from Solution | 371 ppm |
| Formulation# 18 | |
| Benzalkonium Chloride[1] | 617 ppm |
| EDTA[2] | 0.70 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To Balance |
| pH | 9.5 |
| Quat Released from Solution | 576 ppm |

[1]Bardac 208M (81.2% active)
[2]Versene 100 (38% active)
[3]Tergitol 15-S-9 (100% active)
[4]Bardac 4280Z (81.0% active)

The antimicrobial efficacy for each respective formulation was determined according to Germicidal and Detergent Sanitizing Action of Disinfectants Method as described in Chapter 6, Disinfectants, *Official Methods of Analysis of AOAC International*, 16th Edition, 1995 Section 6.3.03, with the modifications set forth above. The carrier dimension, # of carriers wiped, and wiper size were as follows:

| | |
|---|---|
| Carrier Dimension: | 3" × 6" (Formulations 1-14) |
| | 4.5" × 8" (Formulations 15-18) |
| # of Carriers Wiped: | 8 (Formulations 1-5 and 7-13) |
| | 16 (Formulations 15-18) |
| | 8 / 16 (two carrier sizes used) |
| | (Formulation 6) |
| Wiper Size: | 12" × 12" (Formulations 1-5, 7, and 8-18) |
| | 12" × 12" / 6" × 8" (two wiper sizes used) |
| | (Formulation 6) |

The results are set forth below in Table I.

TABLE I

Antimicrobial Efficacy of Formulations 1-18

| Formulation | % Reduction in *S. Aureus* | % Reduction in *E. Coli* |
|---|---|---|
| 1 | >99.994 | Not determined |
| 2 | >99.960 | Not determined |
| 3 | >99.702 | Not determined |
| 4 | >99.860 | Not determined |
| 5 | >99.962 | Not determined |
| 6 | >99.999 (12" × 12") (8 carriers) | >99.955 (12" × 12") (8 carriers) |
| | >99.984 (12" × 12") (16 carriers) | >99.608 (12" × 12") (16 carriers) |
| | | 94.772 (6" × 8") (8 carriers) |
| 7 | 99.992 | Not determined |
| 8 | Not determined | >99.875 |
| 9 | Not determined | 99.246 |
| 10 | Not determined | >99.993 |
| 11 | Not determined | >99.999 |
| 12 | Not determined | 99.993 |
| 13 | Not determined | 99.989 |
| 14 | Not determined | >99.999 |
| 15 | Not determined | >99.999 |
| 16 | Not determined | 99.997 |

TABLE I-continued

Antimicrobial Efficacy of Formulations 1-18

| Formulation | % Reduction in *S. Aureus* | % Reduction in *E. Coli* |
|---|---|---|
| 17 | Not determined | >99.997 |
| 18 | Not determined | 99.9989 |

Thus, as indicated by the results set forth in Table I, wipers formed according to the present invention were capable of providing good antimicrobial efficacy for both gram negative and positive bacteria.

EXAMPLE 2

The ability to form a wiper having good antimicrobial efficacy was demonstrated. In particular, a roll wipers formed from a hydroentangled fabric having a basis weight of 54 gsm (available under the trade name HYDROKNIT® from Kimberly-Clark Corp.) was initially provided. The wipers were then saturated (by hand) with sanitizing Formulations 19-37 (set forth below) in an amount of 475% by weight of the wiper.

| Component | Active Concentration |
|---|---|
| Formulation# 19 | |
| Benzalkonium Chloride[1] | 367 ppm |
| EDTA[2] | 0.45 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To balance |
| pH | 9.1 |
| Formulation# 20 | |
| Benzalkonium Chloride[1] | 1086 ppm |
| EDTA[2] | 0.02 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To balance |
| pH | 6.3 |
| Formulation# 21 | |
| Benzalkonium Chloride[1] | 415 ppm |
| EDTA[2] | 0.70 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To balance |
| pH | 9.5 |
| Formulation# 22 | |
| Benzalkonium Chloride[1] | 417 ppm |
| EDTA[2] | 0.02 wt. % |
| Nonionic Surfactant[3] | 0.50 wt. % |
| Ethanol | 5.00 wt. % |
| Propylene Glycol | 5.00 wt. % |
| Citric Acid | 1.00 wt. % |
| Water | To balance |
| pH | 2.6 |
| Formulation# 23 | |
| Benzalkonium Chloride[1] | 945 ppm |
| Water | To balance |
| pH (NaOH drops) | 9.0 |
| Formulation# 24 | |
| Benzalkonium Chloride[1] | 943 ppm |
| Water | To balance |
| pH (NaOH drops) | 11.0 |
| Formulation# 25 | |
| Benzalkonium Chloride[1] | 945 ppm |
| EDTA[2] | 1.00 wt. % |
| Nonionic Surfactant[3] | 0.01 wt. % |
| Water | To balance |
| pH | 11.4 |
| Formulation# 26 | |
| Benzalkonium Chloride[1] | 2771 ppm |
| Methyl Paraben | 0.10 wt. % |
| Propyl Paraben | 0.04 wt. % |
| Propylene Glycol | 5.00 wt. % |
| Water | To balance |
| pH (Sodium meta silicate drops) | 11.0 |
| Formulation# 27 | |
| Benzalkonium Chloride[1] | 1001 ppm |
| EDTA[2] | 0.30 wt. % |
| Nonionic Surfactant[3] | 0.01 wt. % |
| Water | To balance |
| pH | 11.1 |
| Formulation# 28 | |
| Benzalkonium Chloride[1] | 2620 ppm |
| Methyl Paraben | 0.10 wt. % |
| Propyl Paraben | 0.04 wt. % |
| Propylene Glycol | 5.00 wt. % |
| Water | To balance |
| pH (NaOH drops) | 11.0 |
| Formulation# 29 | |
| Benzalkonium Chloride[1] | 2748 ppm |
| Methyl Paraben | 0.10 wt. % |
| Propyl Paraben | 0.04 wt. % |
| Propylene Glycol | 5.00 wt. % |
| Water | To balance |
| pH (sodium metasilicate) | 11.1 |
| Formulation# 30 | |
| Benzalkonium Chloride[1] | 981 ppm |
| EDTA[2] | 1.00 wt. % |
| Nonionic Surfactant[3] | 0.05 wt. % |
| Water | To balance |
| pH | 11.4 |
| Formulation# 31 | |
| Benzalkonium Chloride[1] | 763 ppm |
| EDTA[2] | 1.00 wt. % |
| Nonionic Surfactant[3] | 0.10 wt. % |
| Water | To balance |
| pH | 11.4 |
| Formulation# 32 | |
| Benzalkonium Chloride[1] | 601 ppm |
| EDTA[2] | 1.00 wt. % |
| Nonionic Surfactant[3] | 0.20 wt. % |

-continued

| Component | Active Concentration |
|---|---|
| Water | To balance |
| pH | 11.4 |

Formulation# 33

| | |
|---|---|
| Benzalkonium Chloride[1] | 415 ppm |
| EDTA[2] | 1.00 wt. % |
| Nonionic Surfactant[3] | 0.50 wt. % |
| Water | To balance |
| pH | 11.4 |

Formulation# 34

| | |
|---|---|
| Benzalkonium Chloride[1] | 1946 ppm |
| EDTA[2] | 0.45 wt. % |
| Ethanol | 10.0 wt. % |
| Methyl Paraben | 0.10 wt. % |
| Propyl Paraben | 0.04 wt. % |
| Water | To balance |
| pH | 9.1 |

Formulation# 35

| | |
|---|---|
| Benzalkonium Chloride[1] | 1993 ppm |
| Ethanol | 10.0 wt. % |
| Methyl Paraben | 0.10 wt. % |
| Propyl Paraben | 0.04 wt. % |
| Sodium Meta Silicate | 1.50 wt. % |
| Water | To balance |
| pH | 9.1 |

Formulation# 36

| | |
|---|---|
| Benzalkonium Chloride[1] | 1997 ppm |
| EDTA[2] | 0.15 wt. % |
| Ethanol | 10.0 wt. % |
| Methyl Paraben | 0.10 wt. % |
| Propyl Paraben | 0.04 wt. % |
| Sodium Meta Silicate | 0.90 wt. % |
| Water | To balance |
| pH | 9.2 |

Formulation# 37

| | |
|---|---|
| Benzalkonium Chloride[1] | 1981 ppm |
| EDTA[2] | 0.15 wt. % |
| Ethanol | 10.0 wt. % |
| Methyl Paraben | 0.10 wt. % |
| Propyl Paraben | 0.04 wt. % |
| Water | To balance |
| pH (NaOH drops) | 9.1 |

[1]Bardac 208 M (81.2% active)
[2]Versene 100 (38% active)
[3]Tergitol 15-S-9 (100% active)

The antimicrobial efficacy for each respective formulation was determined according to Germicidal and Detergent Sanitizing Action of Disinfectants Method as described in Chapter 6, Disinfectants, *Official Methods of Analysis of AOAC International*, 16th Edition, 1995 Section 6.3.03, with the modifications set forth above.

For measuring *E. Coli*, the carrier dimension, # of carriers wiped, and wiper size were as follows:

| | |
|---|---|
| Carrier Dimension: | 4.5" × 8" (Formulations 19-37) |
| # of Carriers Wiped: | 4 (Formulations 26 and 30-37) |
| | 8 (Formulation 29) |
| | 16 (Formulations 19-25 and 27-28) |
| Wiper Size: | 10" × 12" (Formulations 19-20) |
| | 12" × 12" (Formulations 21-37) |

For measuring *S. Aureus*, the carrier dimension, # of carriers wiped, and wiper size were as follows:

Carrier Dimension: 4.5"×8" (Formulations 22, 24-26, and 29-37)

# of Carriers Wiped:

4 (Formulations 26 and 30-37)

8 (Formulations 24 (tested twice) and 29)

16 (Formulations 22 and 24-25)

Wiper Size: 12"×12" (Formulations 22, 24-26, and 29-37)

In addition, the Kill Efficiency Ratio (KER) and Antimicrobial Reduction for *E. Coli* and *S. Aureus* were also determined according to the method set forth above. The results are set forth below in Tables II and IIII.

TABLE II

Antimicrobial Efficacy (*E. Coli*)

| Formulation | % Reduction | Conc. of Quat Released in Solution (ppm) | AM Reduction (%) | KER |
|---|---|---|---|---|
| 19 | 99.9960 | 351 | 4 | 301 |
| 20 | 97.9300 | 388 | 64 | 100 |
| 21 | 99.9980 | 458 | −10 | 328 |
| 22 | 99.9740 | 415 | 0 | 134 |
| 23 | 99.9980 | 410 | 57 | 169 |
| 24 | 99.9996 | 321 | 66 | 92 |
| 25 | 99.9997 | 339 | 64 | 91 |
| 26 | 99.9970 | 402 | 85 | 10 |
| 27 | 99.9920 | 386 | 61 | 97 |
| 28 | 99.9950 | 432 | 84 | 37 |
| 29 | 99.9970 | 373 | 86 | 20 |
| 30 | 99.9990 | 380 | 61 | 257 |
| 31 | 99.9980 | 400 | 48 | 330 |
| 32 | 99.9986 | 421 | 30 | 419 |
| 33 | 99.9988 | 418 | −1 | 607 |
| 34 | 99.9991 | 445 | 77 | 18 |
| 35 | 99.9310 | 396 | 80 | 18 |
| 36 | 99.9870 | 461 | 77 | 18 |
| 37 | 99.9970 | 456 | 77 | 18 |

TABLE III

Antimicrobial Efficacy (*S. Aureus*)

| Formulation | % Reduction | Conc. of Quat Released in Solution (ppm) | AM Reduction (%) | KER |
|---|---|---|---|---|
| 22 | 97.1290 | 415 | 0 | 71 |
| 24 | 99.9972 | 379 | 60 | 373 |
| 25 | 99.9979 | 359 | 62 | 372 |
| 26 | 99.9970 | 400 (16 carriers) | 85 (16 carriers) | 46 (16 carriers) |
| | | 402 (8 carriers) | 58 (8 carriers) | 271 (8 carriers) |
| 29 | 99.9970 | 373 | 86 | 93 |
| 30 | 99.9980 | 380 | 61 | 102 |
| 31 | 99.9970 | 400 | 48 | 131 |
| 32 | 99.9980 | 421 | 30 | 166 |
| 33 | 99.9980 | 418 | −1 | 241 |
| 34 | 99.9900 | 445 | 77 | 3 |
| 35 | 99.9940 | 396 | 80 | 3 |
| 36 | 99.9950 | 461 | 77 | 3 |
| 37 | 99.9900 | 456 | 77 | 3 |

Thus, as indicated by the results set forth above, wipers formed according to the present invention were capable of providing good antimicrobial efficacy for both gram negative and positive bacteria. In addition, such wipers were also capable of providing a relatively high KER and a relatively low expressed antimicrobial agent concentration.

EXAMPLE 3

The ability to form a wiper having good antimicrobial efficacy was demonstrated. In particular, a roll wipers formed from a hydroentangled fabric having a basis weight of 54 gsm (available under the trade name HYDROKNIT® from Kimberly-Clark Corp.) was initially provided. The wipers were then saturated (by hand) with sanitizing Formulations 38-49 (set forth below). Each respective formulation was applied to a single wiper in an amount of 475% by weight of the wiper.

| Component | Active Concentration |
|---|---|
| Formulation# 38 | |
| Benzalkonium Chloride[1] | 380 ppm |
| EDTA[2] | 1.3 wt. % |
| Nonionic Surfactant[3] | 0.50 wt. % |
| Methyl Paraben | 0.10 wt. % |
| Propyl Paraben | 0.04 wt. % |
| Ethanol | 10.0 wt. % |
| Water | To balance |
| PH | 9.7 |
| Formulation# 39 | |
| Benzalkonium Chloride[1] | 385 ppm |
| EDTA[2] | 0.70 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To balance |
| pH | 6.6 |
| Formulation# 40 | |
| Benzalkonium Chloride[1] | 854 ppm |
| EDTA[2] | 0.02 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To balance |
| pH | 9.1 |
| Formulation# 41 | |
| Benzalkonium Chloride[1] | 384 ppm |
| EDTA[2] | 0.45 wt. % |
| Nonionic Surfactant[3] | 0.50 wt. % |
| Methyl Paraben | 0.10 wt. % |
| Propyl Paraben | 0.04 wt. % |
| Propylene Glycol | 5.00 wt. % |
| Water | To balance |
| pH | 9.0 |
| Formulation# 42 | |
| Benzalkonium Chloride[1] | 938 ppm |
| Water | To balance |
| pH (NaOH drops) | 9.1 |
| Formulation# 43 | |
| Benzalkonium Chloride[1] | 943 ppm |
| Water | To balance |
| pH (NaOH drops) | 11.1 |
| Formulation# 44 | |
| Benzalkonium Chloride[1] | 944 ppm |
| Water | To balance |
| pH (sodium meta silicate) | 11.0 |

-continued

| Component | Active Concentration |
|---|---|
| Formulation# 45 | |
| Benzalkonium Chloride[1] | 938 ppm |
| EDTA[2] | 1.0 wt. % |
| Nonionic Surfactant[3] | 0.01 wt. % |
| Water | To balance |
| pH | 11.4 |
| Formulation# 46 | |
| Benzalkonium Chloride[1] | 463 ppm |
| Ethanol | 30.0 wt. % |
| Water | To balance |
| pH | 11.0 |
| Formulation# 47 | |
| Benzalkonium Chloride[1] | 419 ppm |
| Ethanol | 30.0 wt. % |
| Propylene Glycol | 5.00 wt. % |
| Water | To balance |
| pH (NaOH drops) | 11.0 |
| Formulation# 48 | |
| Benzalkonium Chloride[1] | 941 ppm |
| EDTA[2] | 0.02 wt. % |
| Nonionic Surfactant[3] | 0.01 wt. % |
| Water | To balance |
| pH (NaOH drops) | 11.1 |
| Formulation# 49 | |
| Benzalkonium Chloride[1] | 2771 ppm |
| Methyl Paraben | 0.10 wt. % |
| Propyl Paraben | 0.04 wt. % |
| Water | To balance |
| pH | 11.0 |

[1]Bardac 208 M (81.2% active)
[2]Versene 100 (38% active)
[3]Tergitol 15-S-9 (100% active)

The antimicrobial efficacy for each respective formulation was determined according to Germicidal and Detergent Sanitizing Action of Disinfectants Method as described in Chapter 6, Disinfectants, *Official Methods of Analysis of AOAC International*, 16th Edition, 1995 Section 6.3.03, with the modifications set forth above. For measuring *E. Coli*, the carrier dimension, # of carriers wiped, and wiper size were as follows:

| Carrier Dimension: | 4.5" × 8" (Formulations 38-49) |
|---|---|
| # of Carriers Wiped: | 4 (Formulations 38-40) |
| | 8 (Formulations 41-49) |
| Wiper Size: | 6" × 8" (Formulations 38-49) |

In addition, Antimicrobial Reduction was also determined according to the method set forth above. The results are set forth below in Table IV.

TABLE IV

Antimicrobial Efficacy of Formulations 38-49

| Formulation | % Reduction in E. Coli | Concentratio of Quat Released in Solution (ppm) | AM Reduction (%) |
|---|---|---|---|
| 38 | 99.9330 | 391 | −3 |
| 39 | 99.9480 | 412 | −7 |
| 40 | 90.9000 | 198 | 77 |
| 41 | 98.9170 | 400 | −4 |
| 42 | 99.9980 | 392 | 58 |
| 43 | 99.9997 | 321 | 66 |
| 44 | 99.9910 | 397 | 58 |
| 45 | 99.9999 | 339 | 64 |
| 46 | 99.9500 | 376 | 19 |
| 47 | 99.9030 | 401 | 4 |
| 48 | 99.9980 | 339 | 64 |
| 49 | 99.9996 | 402 | 85 |

Thus, for example, wipers formed according to the present invention were capable of providing good antimicrobial efficacy and a relatively low expressed antimicrobial agent concentration.

EXAMPLE 4

The effect of a nonionic surfactant on the kill efficacy and/or Kill Efficiency Ratio of a sanitizing formulation was demonstrated. Wipers formed from a hydroentangled fabric having a basis weight of 54 gsm (available under the trade name HYDROKNIT® from Kimberly-Clark Corp.) were initially provided. The wipers were then saturated (by hand) with various sanitizing formulations (set forth below) in an amount of 475% by weight of the wiper. Each sanitizing formulation contained 0.04% to 0.1 active % by weight antimicrobial agent (provided by Bardac® 208M (81.2% active)).

The antimicrobial efficacy for each respective sample was determined according to Germicidal and Detergent Sanitizing Action of Disinfectants Method as described in Chapter 6, Disinfectants, *Official Methods of Analysis of AOAC International*, 16$^{th}$ Edition, 1995 Section 6.3.03, with the modifications set forth above. For Samples 1-5 and 11-12, kill efficacy of *E. coli* was tested. For Samples 6-10, kill efficacy of *S. Aureus* was tested.

The carrier dimension, # of carriers wiped, and wiper size were as follows:

| | |
|---|---|
| Carrier Dimension: | 4.5" × 8" (Samples 1-12) |
| # of Carriers Wiped: | 4 (Samples 1-10 and 12) |
| | 16 (Sample 11) |
| Wiper Size: | 10" × 12" (Sample 11) |
| | 12" × 12" (Samples 1-10 and 12) |

In addition, the Kill Efficiency Ratio (KER) and Antimicrobial Reduction were also determined according to the method set forth above.

The results are provided below in Tables V-VII.

TABLE V

Samples 1-5

| Sample | pH | EDTA (wt %) | Surfactant (wt %) | Efficacy | Concentration of Quat Released in Solution (ppm) | AM Reduction | KER |
|---|---|---|---|---|---|---|---|
| 1 | 11.4 | 1 | 0.50 | 99.9988 | 418 | −1 | 607 |
| 2 | 11.4 | 1 | 0.20 | 99.9986 | 421 | 30 | 419 |
| 3 | 11.4 | 1 | 0.10 | 99.9980 | 400 | 48 | 330 |
| 4 | 11.4 | 1 | 0.05 | 99.9990 | 380 | 61 | 257 |
| 5 | 11.4 | 1 | 0.01 | 99.9997 | 339 | 64 | 40 |

TABLE VI

Samples 6-10

| Sample | pH | EDTA (wt %) | Surfactant (wt %) | Efficacy | Concentration of Quat Released in Solution (ppm) | AM Reduction | KER |
|---|---|---|---|---|---|---|---|
| 6 | 11.4 | 1 | 0.50 | 99.9980 | 418 | −1 | 241 |
| 7 | 11.4 | 1 | 0.20 | 99.9980 | 421 | 30 | 166 |
| 8 | 11.4 | 1 | 0.10 | 99.9970 | 400 | 48 | 131 |
| 9 | 11.4 | 1 | 0.05 | 99.9980 | 380 | 61 | 102 |
| 10 | 11.4 | 1 | 0.01 | 99.9979 | 359 | 62 | 93 |

TABLE VII

Samples 11-12

| Sample | pH | EDTA (wt %) | Surfactant (wt %) | Methyl Paraben (wt %) | Propyl Paraben (wt %) | Ethanol (wt %) | Propylene Glycol (wt %) | Efficacy | Conc. of Quat in Solution (ppm) | AM Red | KER |
|---|---|---|---|---|---|---|---|---|---|---|---|
| 11 | 9.1 | 0.45 | 0.5 | 0.1 | 0.04 | 0 | 5 | 99.9960 | 351 | 4 | 301 |
| 12 | 9.1 | 0.45 | 0.0 | 0.1 | 0.04 | 10 | 0 | 99.9991 | 445 | 77 | 18 |

Thus, for example, the presence of a nonionic surfactant can, in some embodiments, enhance the KER of the sanitizing formulation.

EXAMPLE 5

The effect of pH and/or a sequestrant on the kill efficacy and Kill Efficiency Ratio of a sanitizing formulation was demonstrated. Wipers formed from a hydroentangled fabric having a basis weight of 54 gsm (available under the trade name HYDROKNIT® from Kimberly-Clark Corp.) were initially provided. The wipers were then saturated (by hand) with various sanitizing formulations (set forth below) in an amount of 475% by weight of the wiper. Each sanitizing formulation contained between 0.04-0.1 active % by weight of antimicrobial agent (provided as Bardac® 208M (81.2% active)).

The kill efficacy (*E. Coli*), KER, and Antimicrobial Reduction were determined as set forth in Example 4. The carrier dimension, # of carriers wiped, and wiper size were as follows:

| | |
|---|---|
| Carrier Dimension: | 4.5" × 8" (Samples 13-15) |
| #of Carriers Wiped: | 16 (Samples 13-15) |
| Wiper Size: | 10" × 12" (Samples 14-15) |
| | 12" × 12" (Sample 13) |

The results are provided below in Table VIII.

Thus, for example, pH can effect the kill efficacy and KER of a sanitizing formulation. For example, in the embodiments set forth in Table VIII, both kill efficacy and KER increased as the pH of the formulation was raised. In addition, the presence of a sequestrant can also effect the kill efficacy and KER of a disinfectant formulation. For example, in the embodiments set forth in Table VIII, both kill efficacy and KER increased as the level of sequestrant was raised.

EXAMPLE 6

The effect of a preservative and/or non-aqueous solvent on the kill efficacy of a sanitizing formulation was demonstrated. Wipers formed from a hydroentangled fabric having a basis weight of 54 gsm (available under the trade name HYDROKNIT® from Kimberly-Clark Corp.) were initially provided. The wipers were then saturated (by hand) with various sanitizing formulations (set forth below) in an amount of 475% by weight of the wiper. Each sanitizing formulation contained between 0.09% to 0.3 active % by weight of antimicrobial agent (provided as Bardac® 208M (81.2% active)).

The kill efficacy (*E. Coli*), KER, and Antimicrobial Reduction were determined as set forth in Example 4. The carrier dimension, # of carriers wiped, and wiper size were as follows:

| | |
|---|---|
| Carrier Dimension: | 4.5" × 8" (Samples 16-19) |
| # of Carriers Wiped: | 4 (Samples 18-19) |
| | 16 (Sample 16-17) |
| Wiper Size: | 6" × 8" (Samples 18-19) |
| | 12" × 12" (Samples 16-17) |

TABLE VIII

Samples 13-15

| Sample | pH | EDTA (wt %) | Surfactant (wt %) | Methyl Paraben (wt %) | Propyl Paraben (wt %) | Propylene Glycol (wt %) | Efficacy | Conc. of Quat in Solution (ppm) | AM Reduction | KER |
|---|---|---|---|---|---|---|---|---|---|---|
| 13 | 9.5 | 0.7 | 0.5 | 0.1 | 0.04 | 5 | 99.9980 | 458 | −10 | 328 |
| 14 | 9.1 | 0.45 | 0.5 | 0.1 | 0.04 | 5 | 99.9960 | 351 | 4 | 301 |
| 15 | 6.3 | 0.02 | 0.5 | 0.1 | 0.04 | 5 | 97.9300 | 388 | 64 | 100 |

The results are provided below in Tables IX-X.

TABLE IX

Samples 16-17

| Sample | pH | Methyl Paraben (wt %) | Propyl Paraben (wt %) | Propylene Glycol (wt %) | pH Modifier | Efficacy | Conc. of Quat in Solution (ppm) | AM Reduction | KER |
|---|---|---|---|---|---|---|---|---|---|
| 16 | 11.0 | 0.1 | 0.04 | 5 | NaOH | 99.9950 | 432 | 84 | 37 |
| 17 | 11.0 | 0.0 | 0.00 | 0 | NaOH | 99.9996 | 321 | 66 | 92 |

TABLE X

Samples 18-19

| Sample | pH | Methyl Paraben (wt %) | Propyl Paraben (wt %) | Propylene Glycol (wt %) | pH Modifier | Efficacy | Conc. of Quat in Solution (ppm) | AM Reduction | KER |
|---|---|---|---|---|---|---|---|---|---|
| 18 | 11.0 | 0.1 | 0.04 | 5 | Sodium Meta silicate | 99.9996 | 402 | 85 | 14 |
| 19 | 11.0 | 0.0 | 0.00 | 0 | Sodium Meta silicate | 99.9910 | 397 | 58 | 40 |

Thus, for example, the presence of a preservative can effect the kill efficacy of a sanitizing formulation. For example, in the embodiments set forth in Table X, kill efficacy increased when preservatives were present. In addition, the presence of a non-aqueous solvent can also effect the kill efficacy of a sanitizing formulation. For example, in the embodiments set forth in Table X, the kill efficacy increased when a non-aqueous solvent was present.

EXAMPLE 7

The effect of a non-aqueous solvent on the Kill Efficiency Ratio of a sanitizing formulation was demonstrated. Wipers formed from a hydroentangled fabric having a basis weight of 54 gsm (available under the trade name HYDROKNIT® from Kimberly-Clark Corp.) were initially provided. The wipers were then saturated (by hand) with various sanitizing formulations (set forth below) in an amount of 475% by weight of the wiper. Each sanitizing formulation contained between 0.04% to 0.1 active % by weight of antimicrobial agent (provided as Bardac® 208M (81.2% active)).

The kill efficacy (E. Coli), KER, and Antimicrobial Reduction were determined as set forth in Example 4. The carrier dimension, # of carriers wiped, and wiper size were as follows:

| | |
|---|---|
| Carrier Dimension: | 4.5" × 8" (Samples 20-21) |
| # of Carriers Wiped: | 4 (Samples 20-21) |
| Wiper Size: | 6" × 8" (Samples 20-21) |

The results are provided below in Table XI.

TABLE XI

Samples 20-21

| Sample | pH | Ethanol (wt %) | pH Modifier | Efficacy | Conc. of Quat in Released Solution (ppm) | AM Reduction | KER |
|---|---|---|---|---|---|---|---|
| 20 | 11.0 | 0 | Sodium Meta silicate | 99.9910 | 397 | 58 | 40 |
| 21 | 11.0 | 30 | Sodium Meta silicate | 99.9500 | 376 | 19 | 82 |

Thus, for example, the presence of a non-aqueous solvent can effect the KER of a disinfectant formulation. For instance, in the embodiment set forth in Table XI, the KER increased when the non-aqueous solvent was present.

EXAMPLE 8

The effect of the substrate on the antimicrobial efficacy of a sanitizing formulation was demonstrated. Three substrate samples 22-24 were tested with the sanitizing formulation

44 set forth in Example III at antimicrobial agent active concentrations of 944 ppm, 1031 ppm, and 476 ppm, respectively.

The first substrate sample was a hydroentangled fabric having a basis weight of 54 gsm (available under the trade name HYDROKNIT® from Kimberly-Clark Corp.). The second and third substrate samples were formed from spunbonded webs containing splittable, multicomponent fibers, such as described above. Specifically, the second substrate contained splittable polyethylene/nylon bicomponent fibers and had a basis weight of 50.9 gsm, while the third substrate contained splittable polyethylene/poly(butylene terephthalate) bicomponent fibers and had a basis weight of 67.8 gsm.

The wipers were then saturated (by hand) with various sanitizing formulations (set forth below) in an amount of 475% by weight of the wiper. The kill efficacy (*E. Coli*) and Antimicrobial Reduction were determined as set forth in Example 4. The carrier dimension, # of carriers wiped, and wiper size were as follows:

| Carrier Dimension: | 4.5" × 8" |
|---|---|
| # of Carriers Wiped: | 4 |
| Wiper Size: | 6" × 8" |

The results are provided below in Table XII.

TABLE XII

Samples 22-24

| Sample | Efficacy | Conc. of Quat in Released Solution (ppm) | AM Reduction |
|---|---|---|---|
| 22 | 99.9910 | 397 | 58 |
| 23 | 99.9992 | 358 | 65 |
| 24 | 99.9993 | 382 | 20 |

EXAMPLE 9

The ability to form a wiper having good antimicrobial efficacy was demonstrated. In particular, a roll of wipers formed from a spunbonded web containing splittable, multicomponent fibers of polyethylene and nylon, as described above, was initially provided. The spunbonded web had a basis weight of 50.9 gsm. The wipers were then saturated (by hand) with the sanitizing formulation set forth below in Table XIII in an amount of 475% by weight of the wiper. The sanitizing formulation contained 1031 parts per million active concentration of antimicrobial agent (provided as Bardac® 208M (81.2% active)).

The kill efficacy (*E. Coli*) and Antimicrobial Reduction were determined as set forth in Example 4. The carrier dimension, # of carriers wiped, and wiper size were as follows:

| Carrier Dimension: | 4.5" × 8" |
|---|---|
| # of Carriers Wiped: | 4 |
| Wiper Size: | 4.5" × 8" |

The results are provided below in Table XIII.

TABLE XIII

Sample 25

| Sample | pH | pH Modifier | Efficacy | Conc. of Quat Released in Solution (ppm) | AM Reduction |
|---|---|---|---|---|---|
| 25 | 11.0 | Sodium Meta silicate | 99.9992 | 358 | 65 |

EXAMPLE 10

The ability to form a wiper having good antimicrobial efficacy was demonstrated. In particular, a roll wipers formed from a hydroentangled fabric having a basis weight of 54 gsm (available under the trade name HYDROKNIT® from Kimberly-Clark Corp.) was initially provided. The wipers were then saturated (by hand) with a sanitizing formulation (set forth in Table XIV below) in an amount of 475% by weight of the wiper.

TABLE XIV

Formulation #50

| Component | Active Concentration |
|---|---|
| Benzalkonium Chloride[1] | 981 ppm |
| EDTA[2] | 1.00 wt. % |
| Nonionic Surfactant[3] | 0.05 wt. % |
| Water | To balance |
| pH | 11.4 |

[1]Bardac 208M (81.2% active)
[2]Versene 100 (38% active)
[3]Tergitol 15-S-9 (100% active)

The kill efficacy of *E. Coli* and *S. Aureus*, Antimicrobial Reduction, and Kill Efficiency Ratio were determined as set forth in Example 4. The carrier dimension, # of carriers wiped, and wiper size were as follows:

| Carrier Dimension: | 10.3" × 14" |
|---|---|
| # of Carriers Wiped: | 4 |
| Wiper Size: | 12" × 12" |

The results are provided below in Table XV.

TABLE XV

Kill Efficacy Results

| Sample | *E. Coli* Efficacy | *S. Aureus* Efficacy | Conc. of Quat Released in Solution (ppm) | AM Reduction | KER |
|---|---|---|---|---|---|
| 26 | 99.9999 | Not determined | 380 | 61 | 363 (*E. Coli*) |
| 27 | 99.9999 | Not determined | 380 | 61 | 351 (*E. Coli*) |

TABLE XV-continued

| | | | Kill Efficacy Results | | |
|---|---|---|---|---|---|
| Sample | E. Coli Efficacy | S. Aureus Efficacy | Conc. of Quat Released in Solution (ppm) | AM Reduction | KER |
| 28 | Not determined | 99.9997 | 380 | 61 | 155 (S. Aureus) |
| 29 | Not determined | 99.9999 | 380 | 61 | 73 (S. Aureus) |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A wiper comprising a nonwoven fabric and a sanitizing formulation applied to said nonwoven fabric in an amount from about 150% to about 600% of the dry weight of the wiper, said sanitizing formulation consisting essentially of one or more surfactants, between about 0.01% by weight to about 0.4% by weight of at least one benzalkonium halide, between about 0.01% to about 5.0% by weight of ethylenediaminetetraacetic acid and/or salts thereof, and a solvent;
   wherein the one or more surfactants consist of one or more nonionic surfactants;
   wherein said sanitizing formulation has a pH of greater than about 8 and is configured so that said formulation is released from said nonwoven fabric as a solution during use of the wiper in food service applications, said benzalkonium halide being present within said released solution in an amount less than about 2000 parts per million of said released solution, and wherein the wiper exhibits a Kill Efficiency Ratio for E. Coli, S. Aureus, or both of at least about 100.

2. A wiper as defined in claim 1, wherein said one or more nonionic surfactants are present in an amount between about 0.01% to about 1% by weight of said sanitizing formulation.

3. A wiper as defined in claim 1, wherein the wiper exhibits a Kill Efficiency Ratio for E. Coli, S. Aureus, or both of at least about 200.

4. A wiper as defined in claim 1, wherein said benzalkonium halide is present in an amount of between about 150 to about 400 parts per million of said released solution.

5. A wiper as defined in claim 1, wherein said benzalkonium halide is present in an amount of less than about 400 parts per million of said released solution.

6. A wiper as defined in claim 1, wherein said nonwoven fabric contains cellulosic fibers.

7. A wiper as defined in claim 1, wherein said benzalkonium halide has the following formula:

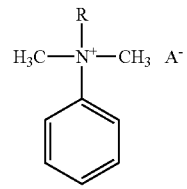

wherein,
R is a $C_8$-$C_{18}$ alkyl group; and
A is a halogen atom.

8. A wiper as defined in claim 1, wherein said solvent includes between about 0.001% to about 30% by weight of non-aqueous solvent.

9. A wiper as defined in claim 1, wherein the pH of said sanitizing formulation is between about 9 to about 12.

10. A wiper as defined in claim 1, wherein the wiper exhibits a log reduction for E. Coli of at least about 3.

11. A wiper as defined in claim 1, wherein the wiper exhibits a log reduction for E. Coli of at least about 4.

12. A wiper as defined in claim 1, wherein the wiper exhibits a log reduction for E. Coli of at least about 5.

13. A wiper as defined in claim 1, wherein the wiper exhibits a log reduction for S. Aureus of at least about 3.

14. A wiper as defined in claim 1, wherein the wiper exhibits a log reduction for S. Aureus of at least about 4.

15. A wiper as defined in claim 1, wherein the wiper exhibits a log reduction for S. Aureus of at least about 5.

16. A wiper as defined in claim 1, wherein the wiper exhibits a Kill Efficiency Ratio for E. Coli, S. Aureus, or both of at least about 100.

17. A wiper as defined in claim 1, wherein the wiper exhibits a Kill Efficiency Ratio for E. Coli, S. Aureus, or both of at least about 400.

18. A wiper as defined in claim 1, wherein said solvent consists of water.

* * * * *